(12) United States Patent
Geneste et al.

(10) Patent No.: US 7,960,386 B2
(45) Date of Patent: Jun. 14, 2011

(54) PYRIDIN-2-ONE COMPOUNDS AND THEIR USE AS MODULATORS OF THE DOPAMINE D3 RECEPTOR

(75) Inventors: Herve Geneste, Neuhofen (DE); Wilfried Braje, Mannheim (DE); Andreas Haupt, Schwetzingen (DE)

(73) Assignee: Abbott GmbH & Co. KG, Wiesbaden (DE)

( * ) Notice: Subject to any disclaimer, the term of this patent is extended or adjusted under 35 U.S.C. 154(b) by 817 days.

(21) Appl. No.: 11/628,633

(22) PCT Filed: Jun. 3, 2005

(86) PCT No.: PCT/EP2005/006001
§ 371 (c)(1),
(2), (4) Date: Sep. 10, 2007

(87) PCT Pub. No.: WO2005/118571
PCT Pub. Date: Dec. 15, 2005

(65) Prior Publication Data
US 2008/0261992 A1 Oct. 23, 2008

(30) Foreign Application Priority Data
Jun. 4, 2004 (DE) .......................... 10 2004 027 359

(51) Int. Cl.
C07D 401/12 (2006.01)
A61K 31/506 (2006.01)
(52) U.S. Cl. .................................. 514/252.14; 544/295
(58) Field of Classification Search ................ 544/295; 514/252.14
See application file for complete search history.

(56) References Cited

U.S. PATENT DOCUMENTS

| 5,958,923 | A | 9/1999 | Hellendahl et al. |
| 6,090,807 | A | 7/2000 | Hellendahl et al. |
| 6,342,604 | B1 | 1/2002 | Hellendahl et al. |
| 2006/0235004 | A1 | 10/2006 | Geneste et al. |

FOREIGN PATENT DOCUMENTS

| WO | WO 96/02246 | 2/1996 |
| WO | WO 03/002543 | 1/2003 |
| WO | WO 2004/080981 | 9/2004 |

OTHER PUBLICATIONS

Le Foll et al., PubMed Abstract (Expert Opinion Investig Drugs, 16(1):45-57), Jan. 2007.*
Layzer, Degenerative Diseases of the Nervous System, Cecil Textbook of Medicine, 20th Edition, vol. 2, pp. 2050-2057, 1996.*
Damasio, Alzheimer's Disease and Related Dementias, Cecil Textbook of Medicine, 20th Edition, vol. 2, pp. 1992-1996, 1996.*
Schwartz, J.C. et al., "The Dopamine D3 Receptor as a Target for Antipsychotics" in H.Y. Meltzer (ed.) Novel Antipsychotic Drugs (Raven Press Ltd., New York 1992), 135-143.
Joyce, J. N., "Dopamine D3 Receptor as a Therapeutic Target for Antipsychotic and Antiparkinsonian Drugs", Pharmacology & Therapeutics 90, 2001, 231-259.
Sokoloff, P. et al., "Localization and Function of the D3 Dopamine Receptor", Arzneim.-Forsch/Drgu Res. 42(1), No. 2a, 1992.
Sokoloff, P. et al., "Molecular Cloning and Characterization of a Novel Dopamine Receptor D3 as a Target for Neuroleptics", Nature 347, 1990, 146-150.
Benoit et al., "Altered Feeding Responses in Mice with Targeted Disruption of the Dopamine-3 Receptor Gene," Behavioral Neuroscience, 2003, vol. 117, No. 1, pp. 46-54.
Joyce, "Dopamine D3 receptor as therapeutic target for antipsychotic and antiparkinsonian drug," Pharmacology & Therapeutics, 2001, vol. 90, pp. 231-259.
Muhlbauer et al., "Dopamine D3 receptors in the rat kidney: role in physiology and pathophysiology," Acta. Physiol. Scand., 2000, vol. 168, pp. 219-223.
Rogoz et al., "Anxiolytic-Like Effects of Preferential Dopamine D3 Receptor Agonists in an Animal Model," Polish Journal of Pharmacology, 2003, vol. 55, pp. 449-454.
Heidbreder et al., "The role of central D3 receptors in drug addiction: a review of pharmacological evidence," Brain Research Reviews, 2005, vol. 49, pp. 77-105.

* cited by examiner

Primary Examiner — Deepak Rao
(74) Attorney, Agent, or Firm — Lisa V. Mueller; Polsinelli Shughart PC

(57) ABSTRACT

The invention relates to pyridin-2-one compounds of general formula (I)

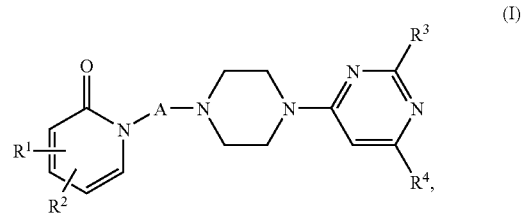

in which
A represents a 4- to 6-membered hydrocarbon chain that can have 1 or 2 methyl groups as substituents, wherein 1 or 2 carbon atoms can be replaced by oxygen, a carbonyl group or sulfur, and the hydrocarbon chain can have a double bond or a triple bond;
$R^1$, $R^2$, $R^3$ and $R^4$ have the meanings as cited in the claims and in the description.
The invention also relates to the tautomers of compounds I and the physiologically acceptable salts of the compounds I and their tautomers.
The invention also relates to the use of these compounds for treating diseases that respond to the influence of dopamine $D_3$ receptor antagonists or agonists.

12 Claims, No Drawings

PYRIDIN-2-ONE COMPOUNDS AND THEIR USE AS MODULATORS OF THE DOPAMINE D3 RECEPTOR

This application is a 371 of PCT/EP2005/006001 filed Jun. 3, 2005.

The present invention relates to novel pyridin-2-one compounds of the general formula I. These compounds have valuable therapeutic properties and are suitable in particular for the treatment of disorders which respond to modulation of the dopamine $D_3$ receptor.

Neurons receive their information inter alia via G protein-coupled receptors. There are numerous substances which exert their effect via these receptors. One of these is dopamine. Confirmed findings about the presence of dopamine and its physiological function as neurotransmitter have been published. Disturbances in the dopaminergic transmitter system result in disorders of the central nervous system which include, for example, schizophrenia, depression or Parkinson's disease. These and other disorders are treated with medicaments which interact with the dopamine receptors.

Until 1990, two subtypes of dopamine receptors were clearly defined pharmacologically, namely the $D_1$ and $D_2$ receptors. More recently, a third subtype has been found, namely the $D_3$ receptor, which appears to mediate some effects of antipsychotics and antiparkinsonian drugs (J. C. Schwartz et al., The Dopamine $D_3$ Receptor as a Target for Antipsychotics, in Novel Antipsychotic Drugs, H. Y. Meltzer, Ed. Raven Press, New York 1992, pages 135-144; M. Dooley et al., Drugs and Aging 1998, 12, 495-514, J. N. Joyce, Pharmacology and Therapeutics 2001, 90, pp. 231-259 "The Dopamine $D_3$-Receptor as a Therapeutic Target for Antipsychotic and Antiparkinsonian Drugs").

Dopamine receptors are now divided into two families. Firstly the $D_2$ group consisting of $D_2$, $D_3$ and $D_4$ receptors, and secondly the $D_1$ group consisting of $D_1$ and $D_5$ receptors. Whereas $D_1$ and $D_2$ receptors are widespread, the expression of $D_3$ receptors by contrast appears to be regioselective. Thus, these receptors are preferentially found in the limbic system, the projecting regions of the mesolimbic dopamine system, especially in the nucleus accumbens, but also in other regions such as amygdala. Because of this comparatively regioselective expression, $D_3$ receptors are regarded as a target with few side effects, and it is assumed that a selective $D_3$ ligand ought to have the properties of known antipsychotics but not their dopamine $D_2$ receptor-mediated neurological side effects (P. Sokoloff et al., Localization and Function of the $D_3$ Dopamine Receptor, *Arzneim. Forsch./Drug Res.* 42(1), 224 (1992); P. Sokoloff et al. Molecular Cloning and Characterization of a Novel Dopamine Receptor ($D_3$) as a Target for Neuroleptics, *Nature*, 347, 146 (1990)).

Pyridinone compounds having dopamine $D_3$ receptor affinity are disclosed in WO 96/02246. These compounds exhibit good affinities for the $D_3$ receptor. They are therefore proposed for the treatment of disorders of the central nervous system. However, the selectivity in relation to other receptors is unsatisfactory.

The invention is therefore based on the object of providing compounds which act as selective dopamine $D_3$ receptor ligands. This object is achieved by pyridin-2-one compounds of the general formula I

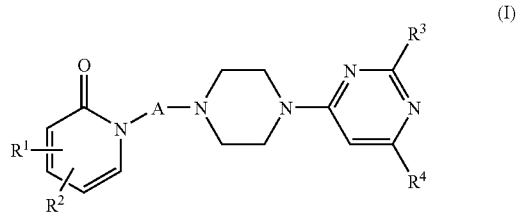

in which
A is a 4- to 6-membered hydrocarbon chain which may have 1 or 2 methyl groups as substituents, in which 1 or 2 carbon atoms may be replaced by oxygen, a carbonyl group or sulfur, and in which the hydrocarbon chain may have a double bond or a triple bond;

$R^1$, $R^2$ are independently of one another hydrogen, CN, $NO_2$, halogen, $OR^5$, $NR^6R^7$, $C(O)NR^6R^7$, $O-C(O)NR^6R^7$, $SR^8$, $SOR^8$, $SO_2R^8$, $SO_2NR^6R^7$, $COOR^9$, $O-C(O)R^{10}$, $COR^{10}$, $C_1$-$C_6$-alkyl, $C_1$-$C_6$-haloalkyl, $C_2$-$C_6$-alkenyl, $C_2$-$C_6$-alkynyl, $C_2$-$C_6$-haloalkenyl, $C_3$-$C_6$-cycloalkyl, 4- to 6-membered heterocyclyl having 1, 2 or 3 heteroatoms selected from O, S and N, which may have 1, 2 or 3 substituents which are selected independently of one another from $C_1$-$C_4$-alkyl, $C_1$-$C_4$-alkoxy, $NR^6R^7$, CN, OH, $C_1$-$C_2$-fluoroalkyl or halogen, phenyl which may have 1, 2 or 3 substituents which are selected independently of one another from $C_1$-$C_4$-alkyl, $C_1$-$C_4$-alkoxy, $NR^6R^7$, OH, CN, $C_1$-$C_2$-fluoroalkyl or halogen, $C_1$-$C_6$-alkyl which has a substituent which is selected from $OR^5$, $NR^6R^7$, $C(O)NR^6R^7$, $O-C(O)NR^6R^7$, $SR^8$, $SOR^8$, $SO_2R^8$, $SO_2NR^6R^7$, $COOR^9$, $O-C(O)R^{10}$, $COR^{10}$, $C_3$-$C_6$-cycloalkyl, 5- or 6-membered heterocyclyl having 1, 2 or 3 heteroatoms selected from O, S and N, and phenyl, where phenyl and heterocyclyl may have 1, 2 or 3 substituents which are selected independently of one another from $C_1$-$C_4$-alkyl, $C_1$-$C_4$-alkoxy, $NR^6R^7$, CN, OH, $C_1$-$C_2$-fluoroalkyl or halogen, $C_2$-$C_6$-alkenyl which has a substituent selected from $OR^5$, $NR^6R^7$, $C(O)NR^6R^7$, $O-C(O)NR^6R^7$, $SR^8$, $SOR^8$, $SO_2R^8$, $SO_2NR^6R^7$, $COOR^9$, $O-C(O)R^{10}$, $COR^{10}$, $C_3$-$C_6$-cycloalkyl, 5- or 6-membered heterocyclyl having 1, 2 or 3 heteroatoms selected from O, S and N, and phenyl, where phenyl and heterocyclyl in turn may have 1, 2 or 3 substituents which are selected independently of one another from $C_1$-$C_4$-alkyl, $C_1$-$C_4$-alkoxy, $NR^6R^7$, OH, CN, $C_1$-$C_2$-fluoroalkyl or halogen;

$R^3$, $R^4$ are independently of one another $OR^5$, $NR^6R^7$, CN, $C_1$-$C_6$-alkyl which is optionally substituted one or more times by OH, $C_1$-$C_4$-alkoxy, halogen or phenyl which in turn may have 1, 2 or 3 substituents selected from $C_1$-$C_4$-alkyl, $C_1$-$C_4$-alkoxy, $NR^6R^7$, OH, CN, $C_1$-$C_2$-fluoroalkyl or halogen, or $C_2$-$C_6$-alkenyl, $C_2$-$C_6$-alkynyl, $C_3$-$C_6$-cycloalkyl, $C_4$-$C_{10}$-bicycloalkyl, $C_6$-$C_{10}$-tricycloalkyl, where the last 5 groups mentioned may optionally be substituted one or more times by halogen or $C_1$-$C_4$-alkyl, or halogen, CN, $C_1$-$C_4$-alkoxy, 5- or 6-membered heterocyclyl having 1, 2 or 3 heteroatoms selected from O, S and N, and phenyl, where phenyl and heterocyclyl may optionally have 1, 2 or 3 substituents which are selected independently of one another from $C_1$-$C_4$-alkyl, $C_1$-$C_4$-alkoxy, $NR^6R^7$, CN, $C_1$-$C_2$-fluoroalkyl and halogen;

$R^5$, $R^6$, $R^7$, $R^8$, $R^9$ and $R^{10}$ are independently of one another H, $C_1$-$C_6$-alkyl which is optionally substituted by OH, $C_1$-$C_4$-alkoxy or phenyl which in turn may have 1, 2 or 3 substituents selected from $C_1$-$C_4$-alkyl, $C_1$-$C_4$-alkoxy, $NR^6R^7$, OH, CN, $C_1$-$C_2$-fluoroalkyl or halogen, or $C_1$-$C_6$-haloalkyl or phenyl which in turn may have 1, 2 or 3 substituents selected from $C_1$-$C_4$-alkyl, $C_1$-$C_4$-alkoxy, $NR^6R^7$, OH, CN, $C_1$-$C_2$-fluoroalkyl or halogen, where $R^7$ may also be a $COR^{11}$ group, and where $R^6$ with $R^7$ may also, together with the nitrogen to which they are bonded, form a 4-, 5- or 6-membered, saturated or unsaturated heterocycle which may have a further heteroatom selected from O, S and $NR^{12}$ as ring member, where $R^{12}$ is hydrogen or $C_1$-$C_4$-alkyl, and which may be substituted by 1, 2, 3 or 4 alkyl groups; and $R^{11}$ is hydrogen, $C_1$-$C_4$-alkyl or phenyl which is optionally substituted by 1, 2 or 3 radicals which are selected independently of one another from $C_1$-$C_4$-alkyl, $C_1$-$C_4$-alkoxy, $NR^6R^7$, CN, $C_1$-$C_2$-fluoroalkyl or halogen;

and the tautomers of the compounds I, the physiologically acceptable salts of the compounds I and the physiologically acceptable salts of the tautomers of the compounds I.

The present invention therefore relates to the compounds of the general formula I, their tautomers and the physiologically tolerated salts of the compounds I and the physiologically acceptable salts of the tautomers of I.

The present invention also relates to the use of compounds of the general formula I and of the tautomers, and to the use of the physiologically acceptable salts of the compounds I and of the tautomers for producing a pharmaceutical composition for the treatment of disorders which respond to influencing by dopamine $D_3$ receptor antagonists or agonists.

The disorders which respond to influencing by dopamine $D_3$ receptor antagonists or agonists include in particular disorders and conditions of the central nervous system, especially affective disorders, neurotic disorders, stress disorders and somatoform disorders and psychoses, specifically schizophrenia and depression and additionally renal function disorders, especially renal function disorders caused by diabetes mellitus (see WO 00/67847).

The aforementioned indications are treated by using according to the invention at least one compound of the general formula I, a tautomer of I, a physiologically acceptable salt of a compound I or a salt of a tautomer of I. If the compounds of the formula I have one or more centers of asymmetry, it is also possible to employ mixtures of enantiomers, especially racemates, mixtures of diastereomers, mixtures of tautomers, but preferably the respective substantially pure enantiomers, diastereomers and tautomers.

Compounds of the formula I which may in particular be in the form of tautomers are those in which one or both of the radicals $R^1$ or $R^2$ is OH or $NHR^6$ in which $R^6$ has the aforementioned meanings.

It is likewise possible to use physiologically acceptable salts of the compounds of the formula I and of the tautomers of I, especially acid addition salts with physiologically tolerated acids. Examples of suitable physiologically tolerated organic and inorganic acids are hydrochloric acid, hydrobromic acid, phosphoric acid, sulfuric acid, $C_1$-$C_4$-alkylsulfonic acids such as methanesulfonic acid, aromatic sulfonic acids such as benzenesulfonic acid and toluenesulfonic acid, oxalic acid, maleic acid, fumaric acid, lactic acid, tartaric acid, adipic acid and benzoic acid. Further acids which can be used are described in Fortschritte der Arzneimittelforschung, volume 10, pages 224 et seq., Birkhäuser Verlag, Basle and Stuttgart, 1966.

Halogen here and hereinafter is fluorine, chlorine, bromine or iodine.

$C_n$-$C_m$-Alkyl (also in radicals such as alkoxy, alkoxyalkyl, alkylthio, alkylamino, dialkylamino, alkylcarbonyl etc.) means a straight-chain or branched alkyl group having n to m carbon atoms, e.g. 1 to 6 and in particular 1 to 4 carbon atoms. Examples of an alkyl group are methyl, ethyl, n-propyl, isopropyl, n-butyl, 2-butyl, isobutyl, tert-butyl, n-pentyl, 2-pentyl, neopentyl, n-hexyl and the like.

The alkyl group may, unless the contrary is indicated, have one or more substituents which are selected independently of one another from OH, $C_1$-$C_4$-alkoxy, halogen and phenyl. In the case of a halogen substituent, the alkyl group may comprise in particular 1, 2, 3 or 4 halogen atoms which may be located on one or more C atoms, preferably in the α or ω position. Groups of this type are also referred to hereinafter as haloalkyl. A preferred haloalkyl is $C_1$-$C_2$-fluoroalkyl or $C_1$-$C_2$-fluorochloroalkyl, in particular $CF_3$, $CHF_2$, $CF_2Cl$, $CH_2F$, $CH_2CF_3$.

In the case of hydroxy-substituted alkyl, the alkyl group has in particular one hydroxy group, such as, for example, hydroxymethyl, 2-hydroxyeth-1-yl, 2-hydroxyprop-1-yl, 3-hydroxyprop-1-yl, 1-hydroxyprop-2-yl, 2-hydroxybut-1-yl, 3-hydroxybut-1-yl, 4-hydroxybut-1-yl, 1-hydroxybut-2-yl, 1-hydroxybut-3-yl, 2-hydroxybut-3-yl, 1-hydroxy-2-methylprop-3-yl, 2-hydroxy-2-methylprop-3-yl or 2-hydroxymethylprop-2-yl, in particular 2-hydroxyethyl.

In the case of alkoxy-substituted alkyl, the alkyl group has in particular one alkoxy substituent. These radicals are referred to, depending on the number of carbon atoms, also as $C_n$-$C_m$-alkoxy-$C_n$-$C_m$-alkyl and are, for example, methoxymethyl, ethoxymethyl, 2-methoxyethyl, 1-methoxyethyl, 2-ethoxyethyl, 1-ethoxyethyl, n-propoxymethyl, isopropoxymethyl, n-butoxymethyl, (1-methylpropoxy)methyl, (2-methylpropoxy)methyl, $CH_2$—$OC(CH_3)_3$, 2-(methoxy)ethyl, 2-(ethoxy)ethyl, 2-(n-propoxy)ethyl, 2-(1-methylethoxy)ethyl, 2-(n-butoxy)ethyl, 2-(1-methylpropoxy)ethyl, 2-(2-methylpropoxy)ethyl, 2-(1,1-dimethylethoxy)ethyl, 2-(methoxy)propyl, 2-(ethoxy)propyl, 2-(n-propoxy)propyl, 2-(1-methylethoxy)propyl, 2-(n-butoxy)propyl, 2-(1-methylpropoxy)propyl, 2-(2-methylpropoxy)propyl, 2-(1,1-dimethylethoxy)propyl, 3-(methoxy)propyl, 3-(ethoxy)propyl, 3-(n-propoxy)propyl, 3-(1-methylethoxy)propyl, 3-(n-butoxy)propyl, 3-(1-methylpropoxy)propyl, 3-(2-methylpropoxy)propyl, 3-(1,1-dimethylethoxy)propyl, 2-(methoxy)butyl, 2-(ethoxy)butyl, 2-(n-propoxy)butyl, 2-(1-methylethoxy)butyl, 2-(n-butoxy)butyl, 2-(1-methylpropoxy)butyl, 2-(2-methylpropoxy)butyl, 2-(1,1-dimethylethoxy)butyl, 3-(methoxy)butyl, 3-(ethoxy)butyl, 3-(n-propoxy)butyl, 3-(1-methylethoxy)butyl, 3-(n-butoxy)butyl, 3-(1-methylpropoxy)butyl, 3-(2-methylpropoxy)butyl, 3-(1,1-dimethylethoxy)butyl, 4-(methoxy)butyl, 4-(ethoxy)butyl, 4-(n-propoxy)butyl, 4-(1-methylethoxy)butyl, 4-(n-butoxy)butyl, 4-(1-methylpropoxy)butyl, 4-(2-methylpropoxy)butyl or 4-(1,1-dimethylethoxy)butyl, preferably methoxymethyl, ethoxymethyl, 2-methoxyethyl, 2-ethoxyethyl, 2-(methoxy)propyl, 2-(ethoxy)propyl or 3-(methoxy)propyl, 3-(ethoxy)propyl.

Cycloalkyl is in particular $C_3$-$C_6$-cycloalkyl such as cyclopropyl, cyclobutyl, cyclopentyl and cyclohexyl. Bicycloalkyl is a bicyclic hydrocarbon radical having 4 to 10 C atoms such as bicyclo[2.1.0]pentyl, bicyclo[2.2.0]hexyl, bicyclo[3.1.0]hexyl, bicyclo[3.2.0]heptyl, bicyclo[2.2.1]heptyl, bicyclo[2.2.2]octyl, bicyclo[3.2.1]octyl and the like. Tricycloalkyl is a tricycloaliphatic radical having 6 to 10 carbon atoms, for example adamantyl.

The term "alkylene" comprises in principle straight-chain or branched radicals having preferably 3 to 10 and particularly preferably 3 to 8 carbon atoms, such as prop-1,2-ylene, prop-1,3-ylene, but-1,2-ylene, but-1,3-ylene, but-1,4-ylene, 2-methylprop-1,3-ylene, pent-1,2-ylene, pent-1,3-ylene, pent-1,4-ylene, pent-1,5-ylene, pent-2,3-ylene, pent-2,4- ylene, 1-methylbut-1,4-ylene, 2-methylbut-1,4-ylene, hex-1,3-ylene, hex-2,4-ylene, hex-1,4-ylene, hex-1,5-ylene, hex-1,6-ylene and the like. $C_0$-Alkylene is a single bond, $C_1$-alkylene is methylene and $C_2$-alkylene is 1,1-ethylene or 1,2-ethylene.

$C_2$-$C_6$-Alkenyl is a mono unsaturated linear or branched hydrocarbon radical having 2, 3, 4, 5 or 6 C atoms, e.g. vinyl, allyl (2-propen-1-yl), 1-propen-1-yl, 2-propen-2-yl, methallyl (2-methylprop-2-en-1-yl) and the like. $C_3$-$C_4$-Alkenyl is in particular allyl, 1-methylprop-2-en-1-yl, 2-buten-1-yl, 3-buten-1-yl or methallyl.

$C_2$-$C_6$-Haloalkenyl is an alkenyl group as defined above in which all or some, e.g. 1, 2, 3, 4 or 5, of the hydrogen atoms are replaced by halogen atoms, in particular by chlorine or fluorine.

$C_2$-$C_6$-Alkynyl is a hydrocarbon radical having 2, 3, 4, 5 or 6 C atoms which has a triple bond, e.g. propargyl (2-propyn-1-yl), 1-methylprop-2-yn-1-yl, 2-butyn-1-yl, 3-butyn-1-yl, 2-pentyn-1-yl, 1-pentyn-3-yl etc.

5- or 6-membered heterocyclyl comprises both aromatic heterocyclyl (hetaryl or heteroaryl) and completely saturated or partially unsaturated heterocyclic radicals. Heterocyclyl has 1, 2 or 3 heteroatoms selected from O, S and N, e.g. 1, 2 or 3 nitrogen atoms, 1 or 2 oxygen atoms, or 1 oxygen atom and 1 or 2 nitrogen atoms or 1 sulfur atom and 1 or 2 nitrogen atoms.

Heterocyclyl may be unsubstituted or have 1, 2 or 3 substituents which are ordinarily selected from $C_1$-$C_4$-alkyl, $C_1$-$C_4$-alkoxy, OH, CN, $NR^6R^7$, $C_1$-$C_2$-fluoroalkyl and halogen.

Examples of saturated heterocyclyl are pyrrolidinyl, piperidinyl, piperazinyl, morpholinyl, oxolanyl, 1,3-dioxolanyl, 1,3- and 1,4-dioxanyl, 1,3-oxothiolanyl, oxazolidinyl and the like.

Examples of "5- or 6-membered aromatic heterocyclic radicals" having 1, 2 or 3 heteroatoms which are selected from O, S and N are in particular pyridinyl, pyrimidinyl, pyrazinyl, triazinyl, imidazolyl, pyrrolyl, pyrazolyl, thienyl, furanyl, oxazolyl, thiazolyl, isoxazolyl, tetrazolyl, thiadiazolyl and triazolyl. These may have 1, 2 or 3 of the aforementioned substituents on the nitrogen atoms and on the carbon atoms. If one of the substituents is hydroxy, the radicals may also be in a tautomeric form with a carbonyl group.

In group A, the two bonding sites are preferably located in the 1,4 position, 1,5 position or 1,6 position. Thus, in the compounds I, the 2-pyridone residue is separated from the piperazine residue preferably by a chain of 4, 5 or 6 atoms. 1 or 2 carbon atoms in the chain A may be replaced by oxygen, sulfur or a carbonyl group. If one or two carbon atoms are replaced by oxygen or sulfur, these heteroatoms are preferably not located at the ends of group A and are in particular not adjacent to one another. A may also have a double or triple bond and/or 1 or 2 methyl groups and is preferably saturated. Examples of radicals A are $CH_2$—$CH_2$—$CH_2$—$CH_2$, $CH_2$—CH=CH—$CH_2$, $CH_2$—C≡C—$CH_2$, $CH_2$—$CH(CH_3)$—$CH_2$—$CH_2$, etc.

With a view to the use of the compounds of the invention as dopamine $D_3$ receptor ligands, the variables A, $R^1$, $R^2$, $R^3$ and $R^4$ preferably have independently of one another the meanings indicated below:

$R^1$ halogen, $OR^5$, $NR^6R^7$, $C_1$-$C_4$-alkyl which is optionally substituted by OH, $C_1$-$C_4$-alkoxy or halogen, or aromatic 5- or 6-membered heterocyclyl having 1, 2 or 3 heteroatoms selected from O, S and N, which may have 1, 2 or 3 substituents which are selected independently of one another from $C_1$-$C_4$-alkyl, $C_1$-$C_4$-alkoxy, $NR^6R^7$, CN, OH, $C_1$-$C_2$-fluoroalkyl or halogen, and phenyl which may have 1, 2 or 3 substituents which are selected independently of one another from $C_1$-$C_4$-alkyl, $C_1$-$C_4$-alkoxy, $NR^6R^7$, OH, CN, $C_1$-$C_2$-fluoroalkyl or halogen.

$R^1$ is in particular selected from optionally substituted phenyl, halogen, OH, $NR^6R^7$, $C_1$-$C_4$-alkoxy and $C_1$-$C_4$-alkyl which is optionally substituted by OH, $C_1$-$C_4$-alkoxy or halogen, particularly preferably from phenyl, OH, halogen, $C_1$-$C_2$-alkoxy, $C_1$-$C_2$-alkyl, $C_1$-$C_2$-fluoroalkyl, and specifically from phenyl, OH, methyl, methoxy and trifluoromethyl;

$R^2$ hydrogen, halogen, CN, $OR^5$, $NR^6R^7$, $SR^8$, and $C_1$-$C_4$-alkyl which is optionally substituted by OH, $C_1$-$C_4$-alkoxy or halogen, and specifically hydrogen;

Preferred compounds I among these are those in which at least one of the radicals $R^1$ or $R^2$ is different from hydrogen. In particular, the compounds I have a substituent $R^1$ different from hydrogen in the 3, 4 or 6 position of the pyridone ring.

$R^3$ $C_1$-$C_6$-alkyl, in particular branched alkyl having 3 to 6 C atoms, or $C_3$-$C_6$-cycloalkyl, particularly preferably tertiary alkyl having 3 to 6 C atoms and specifically tert-butyl.

$R^4$ $C_1$-$C_6$-alkyl, $C_3$-$C_6$-cycloalkyl which optionally has 1 or 2 substituents selected from chlorine and methyl, and $C_1$-$C_2$-fluoroalkyl. In a first particularly preferred embodiment, $R^4$ is $C_1$-$C_2$-fluoroalkyl or $C_2$-$C_6$-alkyl, specifically trifluoromethyl or $C_3$-$C_4$-alkyl such as n-propyl, n-butyl, isopropyl or tert-butyl. $R^4$ is very particularly preferably n-propyl or trifluoromethyl. In another particularly preferred embodiment, $R^4$ is $C_3$-$C_6$-cycloalkyl which optionally has 1 or 2 substituents selected from chlorine and methyl, and in particular is cyclopropyl, cyclobutyl, cyclopentyl or 1-methylcyclopropyl.

A a four-membered hydrocarbon chain which may have 1 or 2 methyl groups as substituents and/or a double bond, in particular butane-1,4-diyl, 2-methylbutane-1,4-diyl, (R)-2-methylbutane-1,4-diyl, (S)-2-methylbutane-1,4-diyl, 2-methylbut-2-ene-1,4-diyl, 3-methylbut-2-ene-1,4-diyl and 3-methylbutane-1,4-diyl, (R)-3-methylbutane-1,4-diyl, (S)-3-methylbutane-1,4-diyl, particularly preferably butane-1,4-diyl.

Moreover, the groups $R^5$, $R^6$, $R^7$, $R^8$, $R^9$, $R^{10}$, $R^{11}$ and $R^{12}$ preferably have the meanings indicated below:

$R^5$ H, $C_1$-$C_4$-alkyl, $CF_3$, $CHF_2$ or phenyl. $OR^5$ is particularly preferably $C_1$-$C_4$-alkoxy, specifically methoxy or ethoxy, trifluoromethoxy or phenoxy.

$R^6$ hydrogen or alkyl.

$R^7$ hydrogen, $C_1$-$C_4$-alkyl, phenyl, benzyl or a group C(O)$R^{11}$. In substituents $CONR^6R^7$, preferably $R^6$ is H or $C_1$-$C_4$-alkyl and preferably $R^7$ is H, $C_1$-$C_4$-alkyl or $COR^{11}$. $CONR^6R^7$ is particularly preferably $CONH_2$, $CONHCH_3$, $CON(CH_3)_2$ or $C(O)NHC(O)CH_3$. In substituents $NR^6R^7$ preferably $R^6$ is H, $C_1$-$C_4$-alkyl or phenyl-substituted $C_1$-$C_4$-alkyl and $R^7$ is H, $C_1$-$C_4$-alkyl or $COR^{11}$. $NR^6R^7$ is particularly preferably $NH_2$, $NHCH_3$, $N(CH_3)_2$, NH-benzyl or $NHCOCH_3$. In substituents $SO_2NR^6R^7$, preferably $R^8$ is H or $C_1$-$C_4$-alkyl and preferably $R^7$ is H, $C_1$-$C_4$-alkyl or $COR^{11}$. $SO_2NR^6R^7$ is particularly preferably sulfamoyl.

In the aforementioned groups, $R^6$ and $R^7$ may also form together with the nitrogen atom to which they are bonded a saturated 5- or 6-membered, preferably saturated nitrogen heterocycle which may have a further heteroatom such as N, S or O and which may be substituted by 1, 2, 3 or 4 alkyl groups. Examples of such heterocycles are piperidinyl, morpholinyl, pyrrolidinyl, 4-methylpiperazinyl and 4-methylpiperidinyl.

$R^8$ H, $C_1$-$C_4$-alkyl, phenyl or benzyl. In substituents $SR^8$, preferably $R^8$ is H, $C_1$-$C_4$-alkyl, phenyl or benzyl. In substituents $SOR^8$, preferably $R^8$ is phenyl or $C_1$-$C_4$-alkyl. In substituents $SO_2R^8$, preferably $R^3$ is H or $C_1$-$C_4$-alkyl. $SO_2R^8$ is particularly preferably methylsulfonyl;

$R^9$ H or $C_1$-$C_4$-alkyl. $COOR^9$ is particularly preferably $C_1$-$C_4$-alkoxycarbonyl such as methoxycarbonyl, ethoxycarbonyl, n-propoxycarbonyl, i-propoxycarbonyl, n-butoxycarbonyl or t-butoxycarbonyl;

$R^{10}$ H, $C_1$-$C_4$-alkyl or phenyl. $COR^{10}$ is particularly preferably formyl, acetyl, propionyl or benzoyl;

$R^{11}$ H, $C_1$-$C_4$-alkyl or phenyl. $COR^{11}$ is particularly preferably formyl, acetyl, propionyl or benzoyl;

$R^{12}$ H or $C_1$-$C_4$-alkyl.

Particularly preferred compounds are those of the formula Ia indicated below

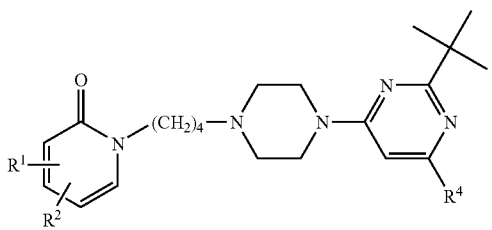

(Ia)

in which $R^1$, $R^2$ and $R^4$ have the meanings mentioned previously and in particular those mentioned as preferred, where $R^1$ is preferably disposed in the 3, 4 or 5 position of the pyridinone ring. Examples of compounds I preferred according to the invention are the compounds of the general formula Ia in which $R^1$, $R^2$ and $R^4$ have the meanings mentioned in each case in one line of table 1.

TABLE 1

|  | $R^1, R^2$ | $R^4$ |
|---|---|---|
| 1. | 3-OH | $CF_3$ |
| 2. | 4-OH | $CF_3$ |
| 3. | 5-OH | $CF_3$ |
| 4. | 3-$CH_3$ | $CF_3$ |
| 5. | 4-$CH_3$ | $CF_3$ |
| 6. | 5-$CH_3$ | $CF_3$ |
| 7. | 3-$OCH_3$ | $CF_3$ |
| 8. | 4-$OCH_3$ | $CF_3$ |
| 9. | 5-$OCH_3$ | $CF_3$ |
| 10. | 3-$N(CH_3)_2$ | $CF_3$ |
| 11. | 4-$N(CH_3)_2$ | $CF_3$ |
| 12. | 5-$N(CH_3)_2$ | $CF_3$ |
| 13. | 3-Cl | $CF_3$ |
| 14. | 4-Cl | $CF_3$ |
| 15. | 5-Cl | $CF_3$ |
| 16. | 3-$CF_3$ | $CF_3$ |
| 17. | 4-$CF_3$ | $CF_3$ |
| 18. | 5-$CF_3$ | $CF_3$ |
| 19. | 3-CN | $CF_3$ |
| 20. | 4-CN | $CF_3$ |
| 21. | 5-CN | $CF_3$ |
| 22. | 3-$H_3C$—O—$CH_2$ | $CF_3$ |
| 23. | 4-$H_3C$—O—$CH_2$ | $CF_3$ |
| 24. | 5-$H_3C$—O—$CH_2$ | $CF_3$ |
| 25. | 6-$CH_3$ | $CF_3$ |
| 26. | 4-tert-Butyl | $CF_3$ |
| 27. | 4-Azetidin-1-yl | $CF_3$ |
| 28. | 4-Pyrrolidin-1-yl | $CF_3$ |
| 29. | 4-Piperidin-1-yl | $CF_3$ |
| 30. | 4-Phenyl | $CF_3$ |
| 31. | 4-(1-Methylpyrrol-2-yl) | $CF_3$ |
| 32. | 4-(3-Pyridyl) | $CF_3$ |
| 33. | 4-(3-Thienyl) | $CF_3$ |
| 34. | 4-(4-Fluorophenyl) | $CF_3$ |
| 35. | 4-(4-Pyridyl) | $CF_3$ |
| 36. | 4-(3-Furyl) | $CF_3$ |
| 37. | 4-(2-Furyl) | $CF_3$ |
| 38. | 4-(2-Pyrrolyl) | $CF_3$ |
| 39. | 4-(2-Thienyl) | $CF_3$ |
| 40. | 4-(Pyridazin-2-yl) | $CF_3$ |
| 41. | 4-(4-Methylthiazol-5-yl) | $CF_3$ |
| 42. | 4-(2-Methyloxazol-4-yl) | $CF_3$ |
| 43. | 4-(Cyclopropyl) | $CF_3$ |
| 44. | 4-(Cyclobutyl) | $CF_3$ |
| 45. | 4-(Cyclopentyl) | $CF_3$ |
| 46. | 4-(Cyclohexyl) | $CF_3$ |
| 47. | 4-(Oxan-4-yl) | $CF_3$ |
| 48. | 4-(1-Methylpiperidin-4-yl) | $CF_3$ |
| 49. | 4-OH, 5-$CF_3$ | $CF_3$ |
| 50. | 4-OH, 5-$CH_3$ | $CF_3$ |
| 51. | 4-OH, 5-$C_2H_5$ | $CF_3$ |
| 52. | 4-OH, 5-CN | $CF_3$ |
| 53. | 4-OH, 5-F | $CF_3$ |
| 54. | 4-OH, 5-Cl | $CF_3$ |
| 55. | 4-OH, 6-$CH_3$ | $CF_3$ |
| 56. | 3-OH | $CHF_2$ |
| 57. | 4-OH | $CHF_2$ |
| 58. | 5-OH | $CHF_2$ |
| 59. | 3-$CH_3$ | $CHF_2$ |
| 60. | 4-$CH_3$ | $CHF_2$ |
| 61. | 5-$CH_3$ | $CHF_2$ |
| 62. | 3-$OCH_3$ | $CHF_2$ |
| 63. | 4-$OCH_3$ | $CHF_2$ |
| 64. | 5-$OCH_3$ | $CHF_2$ |
| 65. | 3-$N(CH_3)_2$ | $CHF_2$ |
| 66. | 4-$N(CH_3)_2$ | $CHF_2$ |
| 67. | 5-$N(CH_3)_2$ | $CHF_2$ |
| 68. | 3-Cl | $CHF_2$ |
| 69. | 4-Cl | $CHF_2$ |
| 70. | 5-Cl | $CHF_2$ |
| 71. | 3-$CF_3$ | $CHF_2$ |
| 72. | 4-$CF_3$ | $CHF_2$ |
| 73. | 5-$CF_3$ | $CHF_2$ |
| 74. | 3-CN | $CHF_2$ |
| 75. | 4-CN | $CHF_2$ |
| 76. | 5-CN | $CHF_2$ |
| 77. | 3-$H_3C$—O—$CH_2$ | $CHF_2$ |
| 78. | 4-$H_3C$—O—$CH_2$ | $CHF_2$ |
| 79. | 5-$H_3C$—O—$CH_2$ | $CHF_2$ |
| 80. | 6-$CH_3$ | $CHF_2$ |
| 81. | 4-tert-Butyl | $CHF_2$ |
| 82. | 4-Azetidin-1-yl | $CHF_2$ |
| 83. | 4-Pyrrolidin-1-yl | $CHF_2$ |
| 84. | 4-Piperidin-1-yl | $CHF_2$ |
| 85. | 4-Phenyl | $CHF_2$ |
| 86. | 4-(1-Methylpyrrol-2-yl) | $CHF_2$ |
| 87. | 4-(3-Pyridyl) | $CHF_2$ |
| 88. | 4-(3-Thienyl) | $CHF_2$ |
| 89. | 4-(4-Fluorophenyl) | $CHF_2$ |
| 90. | 4-(4-Pyridyl) | $CHF_2$ |
| 91. | 4-(3-Furyl) | $CHF_2$ |
| 92. | 4-(2-Furyl) | $CHF_2$ |
| 93. | 4-(2-Pyrrolyl) | $CHF_2$ |
| 94. | 4-(2-Thienyl) | $CHF_2$ |
| 95. | 4-(Pyridazin-2-yl) | $CHF_2$ |
| 96. | 4-(4-Methylthiazol-5-yl) | $CHF_2$ |
| 97. | 4-(2-Methyloxazol-4-yl) | $CHF_2$ |
| 98. | 4-(Cyclopropyl) | $CHF_2$ |
| 99. | 4-(Cyclobutyl) | $CHF_2$ |
| 100. | 4-(Cyclopentyl) | $CHF_2$ |
| 101. | 4-(Cyclohexyl) | $CHF_2$ |
| 102. | 4-(Oxan-4-yl) | $CHF_2$ |
| 103. | 4-(1-Methylpiperidin-4-yl) | $CHF_2$ |
| 104. | 4-OH, 5-$CF_3$ | $CHF_2$ |
| 105. | 4-OH, 5-$CH_3$ | $CHF_2$ |
| 106. | 4-OH, 5-$C_2H_5$ | $CHF_2$ |
| 107. | 4-OH, 5-CN | $CHF_2$ |
| 108. | 4-OH, 5-F | $CHF_2$ |
| 109. | 4-OH, 5-Cl | $CHF_2$ |

TABLE 1-continued

| | $R^1, R^2$ | $R^4$ |
|---|---|---|
| 110. | 4-OH, 6-CH$_3$ | CHF$_2$ |
| 111. | 3-OH | C(CH$_3$)$_3$ |
| 112. | 4-OH | C(CH$_3$)$_3$ |
| 113. | 5-OH | C(CH$_3$)$_3$ |
| 114. | 3-CH$_3$ | C(CH$_3$)$_3$ |
| 115. | 4-CH$_3$ | C(CH$_3$)$_3$ |
| 116. | 5-CH$_3$ | C(CH$_3$)$_3$ |
| 117. | 3-OCH$_3$ | C(CH$_3$)$_3$ |
| 118. | 4-OCH$_3$ | C(CH$_3$)$_3$ |
| 119. | 5-OCH$_3$ | C(CH$_3$)$_3$ |
| 120. | 3-N(CH$_3$)$_2$ | C(CH$_3$)$_3$ |
| 121. | 4-N(CH$_3$)$_2$ | C(CH$_3$)$_3$ |
| 122. | 5-N(CH$_3$)$_2$ | C(CH$_3$)$_3$ |
| 123. | 3-Cl | C(CH$_3$)$_3$ |
| 124. | 4-Cl | C(CH$_3$)$_3$ |
| 125. | 5-Cl | C(CH$_3$)$_3$ |
| 126. | 3-CF$_3$ | C(CH$_3$)$_3$ |
| 127. | 4-CF$_3$ | C(CH$_3$)$_3$ |
| 128. | 5-CF$_3$ | C(CH$_3$)$_3$ |
| 129. | 3-CN | C(CH$_3$)$_3$ |
| 130. | 4-CN | C(CH$_3$)$_3$ |
| 131. | 5-CN | C(CH$_3$)$_3$ |
| 132. | 3-H$_3$C—O—CH$_2$ | C(CH$_3$)$_3$ |
| 133. | 4-H$_3$C—O—CH$_2$ | C(CH$_3$)$_3$ |
| 134. | 5-H$_3$C—O—CH$_2$ | C(CH$_3$)$_3$ |
| 135. | 6-CH$_3$ | C(CH$_3$)$_3$ |
| 136. | 4-tert-Butyl | C(CH$_3$)$_3$ |
| 137. | 4-Azetidin-1-yl | C(CH$_3$)$_3$ |
| 138. | 4-Pyrrolidin-1-yl | C(CH$_3$)$_3$ |
| 139. | 4-Piperidin-1-yl | C(CH$_3$)$_3$ |
| 140. | 4-Phenyl | C(CH$_3$)$_3$ |
| 141. | 4-(1-Methylpyrrol-2-yl) | C(CH$_3$)$_3$ |
| 142. | 4-(3-Pyridyl) | C(CH$_3$)$_3$ |
| 143. | 4-(3-Thienyl) | C(CH$_3$)$_3$ |
| 144. | 4-(4-Fluorophenyl) | C(CH$_3$)$_3$ |
| 145. | 4-(4-Pyridyl) | C(CH$_3$)$_3$ |
| 146. | 4-(3-Furyl) | C(CH$_3$)$_3$ |
| 147. | 4-(2-Furyl) | C(CH$_3$)$_3$ |
| 148. | 4-(2-Pyrrolyl) | C(CH$_3$)$_3$ |
| 149. | 4-(2-Thienyl) | C(CH$_3$)$_3$ |
| 150. | 4-(Pyridazin-2-yl) | C(CH$_3$)$_3$ |
| 151. | 4-(4-Methylthiazol-5-yl) | C(CH$_3$)$_3$ |
| 152. | 4-(2-Methyloxazol-4-yl) | C(CH$_3$)$_3$ |
| 153. | 4-(Cyclopropyl) | C(CH$_3$)$_3$ |
| 154. | 4-(Cyclobutyl) | C(CH$_3$)$_3$ |
| 155. | 4-(Cyclopentyl) | C(CH$_3$)$_3$ |
| 156. | 4-(Cyclohexyl) | C(CH$_3$)$_3$ |
| 157. | 4-(Oxan-4-yl) | C(CH$_3$)$_3$ |
| 158. | 4-(1-Methylpiperidin-4-yl) | C(CH$_3$)$_3$ |
| 159. | 4-OH, 5-CF$_3$ | C(CH$_3$)$_3$ |
| 160. | 4-OH, 5-CH$_3$ | C(CH$_3$)$_3$ |
| 161. | 4-OH, 5-C$_2$H$_5$ | C(CH$_3$)$_3$ |
| 162. | 4-OH, 5-CN | C(CH$_3$)$_3$ |
| 163. | 4-OH, 5-F | C(CH$_3$)$_3$ |
| 164. | 4-OH, 5-Cl | C(CH$_3$)$_3$ |
| 165. | 4-OH, 6-CH$_3$ | C(CH$_3$)$_3$ |
| 166. | 3-OH | cyclo-C$_3$H$_5$ |
| 167. | 4-OH | cyclo-C$_3$H$_5$ |
| 168. | 5-OH | cyclo-C$_3$H$_5$ |
| 169. | 3-CH$_3$ | cyclo-C$_3$H$_5$ |
| 170. | 4-CH$_3$ | cyclo-C$_3$H$_5$ |
| 171. | 5-CH$_3$ | cyclo-C$_3$H$_5$ |
| 172. | 3-OCH$_3$ | cyclo-C$_3$H$_5$ |
| 173. | 4-OCH$_3$ | cyclo-C$_3$H$_5$ |
| 174. | 5-OCH$_3$ | cyclo-C$_3$H$_5$ |
| 175. | 3-N(CH$_3$)$_2$ | cyclo-C$_3$H$_5$ |
| 176. | 4-N(CH$_3$)$_2$ | cyclo-C$_3$H$_5$ |
| 177. | 5-N(CH$_3$)$_2$ | cyclo-C$_4$H$_7$ |
| 178. | 3-Cl | cyclo-C$_3$H$_5$ |
| 179. | 4-Cl | cyclo-C$_3$H$_5$ |
| 180. | 5-Cl | cyclo-C$_3$H$_5$ |
| 181. | 3-CF$_3$ | cyclo-C$_3$H$_5$ |
| 182. | 4-CF$_3$ | cyclo-C$_3$H$_5$ |
| 183. | 5-CF$_3$ | cyclo-C$_3$H$_5$ |
| 184. | 3-CN | cyclo-C$_3$H$_5$ |
| 185. | 4-CN | cyclo-C$_3$H$_5$ |
| 186. | 5-CN | cyclo-C$_3$H$_5$ |
| 187. | 3-H$_3$C—O—CH$_2$ | cyclo-C$_3$H$_5$ |
| 188. | 4-H$_3$C—O—CH$_2$ | cyclo-C$_3$H$_5$ |
| 189. | 5-H$_3$C—O—CH$_2$ | cyclo-C$_3$H$_5$ |
| 190. | 6-CH$_3$ | cyclo-C$_3$H$_5$ |
| 191. | 4-tert-Butyl | cyclo-C$_3$H$_5$ |
| 192. | 4-Azetidin-1-yl | cyclo-C$_3$H$_5$ |
| 193. | 4-Pyrrolidin-1-yl | cyclo-C$_3$H$_5$ |
| 194. | 4-Piperidin-1-yl | cyclo-C$_3$H$_5$ |
| 195. | 4-Phenyl | cyclo-C$_3$H$_5$ |
| 196. | 4-(1-Methylpyrrol-2-yl) | cyclo-C$_3$H$_5$ |
| 197. | 4-(3-Pyridyl) | cyclo-C$_3$H$_5$ |
| 198. | 4-(3-Thienyl) | cyclo-C$_3$H$_5$ |
| 199. | 4-(4-Fluorophenyl) | cyclo-C$_3$H$_5$ |
| 200. | 4-(4-Pyridyl) | cyclo-C$_3$H$_5$ |
| 201. | 4-(3-Furyl) | cyclo-C$_3$H$_5$ |
| 202. | 4-(2-Furyl) | cyclo-C$_3$H$_5$ |
| 203. | 4-(2-Pyrrolyl) | cyclo-C$_3$H$_5$ |
| 204. | 4-(2-Thienyl) | cyclo-C$_3$H$_5$ |
| 205. | 4-(Pyridazin-2-yl) | cyclo-C$_3$H$_5$ |
| 206. | 4-(4-Methylthiazol-5-yl) | cyclo-C$_3$H$_5$ |
| 207. | 4-(2-Methyloxazol-4-yl) | cyclo-C$_3$H$_5$ |
| 208. | 4-(Cyclopropyl) | cyclo-C$_3$H$_5$ |
| 209. | 4-(Cyclobutyl) | cyclo-C$_3$H$_5$ |
| 210. | 4-(Cyclopentyl) | cyclo-C$_3$H$_5$ |
| 211. | 4-(Cyclohexyl) | cyclo-C$_3$H$_5$ |
| 212. | 4-(Oxan-4-yl) | cyclo-C$_3$H$_5$ |
| 213. | 4-(1-Methylpiperidin-4-yl) | cyclo-C$_3$H$_5$ |
| 214. | 4-OH, 5-CF$_3$ | cyclo-C$_3$H$_5$ |
| 215. | 4-OH, 5-CH$_3$ | cyclo-C$_3$H$_5$ |
| 216. | 4-OH, 5-C$_2$H$_5$ | cyclo-C$_3$H$_5$ |
| 217. | 4-OH, 5-CN | cyclo-C$_3$H$_5$ |
| 218. | 4-OH, 5-F | cyclo-C$_3$H$_5$ |
| 219. | 4-OH, 5-Cl | cyclo-C$_3$H$_5$ |
| 220. | 4-OH, 6-CH$_3$ | cyclo-C$_3$H$_5$ |
| 221. | 3-OH | cyclo-C$_4$H$_7$ |
| 222. | 4-OH | cyclo-C$_4$H$_7$ |
| 223. | 5-OH | cyclo-C$_4$H$_7$ |
| 224. | 3-CH$_3$ | cyclo-C$_4$H$_7$ |
| 225. | 4-CH$_3$ | cyclo-C$_4$H$_7$ |
| 226. | 5-CH$_3$ | cyclo-C$_4$H$_7$ |
| 227. | 3-OCH$_3$ | cyclo-C$_4$H$_7$ |
| 228. | 4-OCH$_3$ | cyclo-C$_4$H$_7$ |
| 229. | 5-OCH$_3$ | cyclo-C$_4$H$_7$ |
| 230. | 3-N(CH$_3$)$_2$ | cyclo-C$_4$H$_7$ |
| 231. | 4-N(CH$_3$)$_2$ | cyclo-C$_4$H$_7$ |
| 232. | 5-N(CH$_3$)$_2$ | cyclo-C$_4$H$_7$ |
| 233. | 3-Cl | cyclo-C$_4$H$_7$ |
| 234. | 4-Cl | cyclo-C$_4$H$_7$ |
| 235. | 5-Cl | cyclo-C$_4$H$_7$ |
| 236. | 3-CF$_3$ | cyclo-C$_4$H$_7$ |
| 237. | 4-CF$_3$ | cyclo-C$_4$H$_7$ |
| 238. | 5-CF$_3$ | cyclo-C$_4$H$_7$ |
| 239. | 3-CN | cyclo-C$_4$H$_7$ |
| 240. | 4-CN | cyclo-C$_4$H$_7$ |
| 241. | 5-CN | cyclo-C$_4$H$_7$ |
| 242. | 3-H$_3$C—O—CH$_2$ | cyclo-C$_4$H$_7$ |
| 243. | 4-H$_3$C—O—CH$_2$ | cyclo-C$_4$H$_7$ |
| 244. | 5-H$_3$C—O—CH$_2$ | cyclo-C$_4$H$_7$ |
| 245. | 6-CH$_3$ | cyclo-C$_4$H$_7$ |
| 246. | 4-tert-Butyl | cyclo-C$_4$H$_7$ |
| 247. | 4-Azetidin-1-yl | cyclo-C$_4$H$_7$ |
| 248. | 4-Pyrrolidin-1-yl | cyclo-C$_4$H$_7$ |
| 249. | 4-Piperidin-1-yl | cyclo-C$_4$H$_7$ |
| 250. | 4-Phenyl | cyclo-C$_4$H$_7$ |
| 251. | 4-(1-Methylpyrrol-2-yl) | cyclo-C$_4$H$_7$ |
| 252. | 4-(3-Pyridyl) | cyclo-C$_4$H$_7$ |
| 253. | 4-(3-Thienyl) | cyclo-C$_4$H$_7$ |
| 254. | 4-(4-Fluorophenyl) | cyclo-C$_4$H$_7$ |
| 255. | 4-(4-Pyridyl) | cyclo-C$_4$H$_7$ |
| 256. | 4-(3-Furyl) | cyclo-C$_4$H$_7$ |
| 257. | 4-(2-Furyl) | cyclo-C$_4$H$_7$ |
| 258. | 4-(2-Pyrrolyl) | cyclo-C$_4$H$_7$ |
| 259. | 4-(2-Thienyl) | cyclo-C$_4$H$_7$ |
| 260. | 4-(Pyridazin-2-yl) | cyclo-C$_4$H$_7$ |
| 261. | 4-(4-Methylthiazol-5-yl) | cyclo-C$_4$H$_7$ |
| 262. | 4-(2-Methyloxazol-4-yl) | cyclo-C$_4$H$_7$ |
| 263. | 4-(Cyclopropyl) | cyclo-C$_4$H$_7$ |
| 264. | 4-(Cyclobutyl) | cyclo-C$_4$H$_7$ |
| 265. | 4-(Cyclopentyl) | cyclo-C$_4$H$_7$ |

TABLE 1-continued

| | $R^1, R^2$ | $R^4$ |
|---|---|---|
| 266. | 4-(Cyclohexyl) | cyclo-$C_4H_7$ |
| 267. | 4-(Oxan-4-yl) | cyclo-$C_4H_7$ |
| 268. | 4-(1-Methylpiperidin-4-yl) | cyclo-$C_4H_7$ |
| 269. | 4-OH, 5-$CF_3$ | cyclo-$C_4H_7$ |
| 270. | 4-OH, 5-$CH_3$ | cyclo-$C_4H_7$ |
| 271. | 4-OH, 5-$C_2H_5$ | cyclo-$C_4H_7$ |
| 272. | 4-OH, 5-CN | cyclo-$C_4H_7$ |
| 273. | 4-OH, 5-F | cyclo-$C_4H_7$ |
| 274. | 4-OH, 5-Cl | cyclo-$C_4H_7$ |
| 275. | 4-OH, 6-$CH_3$ | cyclo-$C_4H_7$ |
| 276. | 3-OH | cyclo-$C_5H_9$ |
| 277. | 4-OH | cyclo-$C_5H_9$ |
| 278. | 5-OH | cyclo-$C_5H_9$ |
| 279. | 3-$CH_3$ | cyclo-$C_5H_9$ |
| 280. | 4-$CH_3$ | cyclo-$C_5H_9$ |
| 281. | 5-$CH_3$ | cyclo-$C_5H_9$ |
| 282. | 3-$OCH_3$ | cyclo-$C_5H_9$ |
| 283. | 4-$OCH_3$ | cyclo-$C_5H_9$ |
| 284. | 5-$OCH_3$ | cyclo-$C_5H_9$ |
| 285. | 3-$N(CH_3)_2$ | cyclo-$C_5H_9$ |
| 286. | 4-$N(CH_3)_2$ | cyclo-$C_5H_9$ |
| 287. | 5-$N(CH_3)_2$ | cyclo-$C_5H_9$ |
| 288. | 3-Cl | cyclo-$C_5H_9$ |
| 289. | 4-Cl | cyclo-$C_5H_9$ |
| 290. | 5-Cl | cyclo-$C_5H_9$ |
| 291. | 3-$CF_3$ | cyclo-$C_5H_9$ |
| 292. | 4-$CF_3$ | cyclo-$C_5H_9$ |
| 293. | 5-$CF_3$ | cyclo-$C_5H_9$ |
| 294. | 3-CN | cyclo-$C_5H_9$ |
| 295. | 4-CN | cyclo-$C_5H_9$ |
| 296. | 5-CN | cyclo-$C_5H_9$ |
| 297. | 3-$H_3C$—O—$CH_2$ | cyclo-$C_5H_9$ |
| 298. | 4-$H_3C$—O—$CH_2$ | cyclo-$C_5H_9$ |
| 299. | 5-$H_3C$—O—$CH_2$ | cyclo-$C_5H_9$ |
| 300. | 6-$CH_3$ | cyclo-$C_5H_9$ |
| 301. | 4-tert-Butyl | cyclo-$C_5H_9$ |
| 302. | 4-Azetidin-1-yl | cyclo-$C_5H_9$ |
| 303. | 4-Pyrrolidin-1-yl | cyclo-$C_5H_9$ |
| 304. | 4-Piperidin-1-yl | cyclo-$C_5H_9$ |
| 305. | 4-Phenyl | cyclo-$C_5H_9$ |
| 306. | 4-(1-Methylpyrrol-2-yl) | cyclo-$C_5H_9$ |
| 307. | 4-(3-Pyridyl) | cyclo-$C_5H_9$ |
| 308. | 4-(3-Thienyl) | cyclo-$C_5H_9$ |
| 309. | 4-(4-Fluorophenyl) | cyclo-$C_5H_9$ |
| 310. | 4-(4-Pyridyl) | cyclo-$C_5H_9$ |
| 311. | 4-(3-Furyl) | cyclo-$C_5H_9$ |
| 312. | 4-(2-Furyl) | cyclo-$C_5H_9$ |
| 313. | 4-(2-Pyrrolyl) | cyclo-$C_5H_9$ |
| 314. | 4-(2-Thienyl) | cyclo-$C_5H_9$ |
| 315. | 4-(Pyridazin-2-yl) | cyclo-$C_5H_9$ |
| 316. | 4-(4-Methylthiazol-5-yl) | cyclo-$C_5H_9$ |
| 317. | 4-(2-Methyloxazol-4-yl) | cyclo-$C_5H_9$ |
| 318. | 4-(Cyclopropyl) | cyclo-$C_5H_9$ |
| 319. | 4-(Cyclobutyl) | cyclo-$C_5H_9$ |
| 320. | 4-(Cyclopentyl) | cyclo-$C_5H_9$ |
| 321. | 4-(Cyclohexyl) | cyclo-$C_5H_9$ |
| 322. | 4-(Oxan-4-yl) | cyclo-$C_5H_9$ |
| 323. | 4-(1-Methylpiperidin-4-yl) | cyclo-$C_5H_9$ |
| 324. | 4-OH, 5-$CF_3$ | cyclo-$C_5H_9$ |
| 325. | 4-OH, 5-$CH_3$ | cyclo-$C_5H_9$ |
| 326. | 4-OH, 5-$C_2H_5$ | cyclo-$C_5H_9$ |
| 327. | 4-OH, 5-CN | cyclo-$C_5H_9$ |
| 328. | 4-OH, 5-F | cyclo-$C_5H_9$ |
| 329. | 4-OH, 5-Cl | cyclo-$C_5H_9$ |
| 330. | 4-OH, 6-$CH_3$ | cyclo-$C_5H_9$ |
| 331. | 3-OH | $CH_3$ |
| 332. | 4-OH | $CH_3$ |
| 333. | 5-OH | $CH_3$ |
| 334. | 3-$CH_3$ | $CH_3$ |
| 335. | 4-$CH_3$ | $CH_3$ |
| 336. | 5-$CH_3$ | $CH_3$ |
| 337. | 3-$OCH_3$ | $CH_3$ |
| 338. | 4-$OCH_3$ | $CH_3$ |
| 339. | 5-$OCH_3$ | $CH_3$ |
| 340. | 3-$N(CH_3)_2$ | $CH_3$ |
| 341. | 4-$N(CH_3)_2$ | $CH_3$ |
| 342. | 5-$N(CH_3)_2$ | $CH_3$ |
| 343. | 3-Cl | $CH_3$ |
| 344. | 4-Cl | $CH_3$ |
| 345. | 5-Cl | $CH_3$ |
| 346. | 3-$CF_3$ | $CH_3$ |
| 347. | 4-$CF_3$ | $CH_3$ |
| 348. | 5-$CF_3$ | $CH_3$ |
| 349. | 3-CN | $CH_3$ |
| 350. | 4-CN | $CH_3$ |
| 351. | 5-CN | $CH_3$ |
| 352. | 3-$H_3C$—O—$CH_2$ | $CH_3$ |
| 353. | 4-$H_3C$—O—$CH_2$ | $CH_3$ |
| 354. | 5-$H_3C$—O—$CH_2$ | $CH_3$ |
| 355. | 6-$CH_3$ | $CH_3$ |
| 356. | 4-tert-Butyl | $CH_3$ |
| 357. | 4-Azetidin-1-yl | $CH_3$ |
| 358. | 4-Pyrrolidin-1-yl | $CH_3$ |
| 359. | 4-Piperidin-1-yl | $CH_3$ |
| 360. | 4-Phenyl | $CH_3$ |
| 361. | 4-(1-Methylpyrrol-2-yl) | $CH_3$ |
| 362. | 4-(3-Pyridyl) | $CH_3$ |
| 363. | 4-(3-Thienyl) | $CH_3$ |
| 364. | 4-(4-Fluorophenyl) | $CH_3$ |
| 365. | 4-(4-Pyridyl) | $CH_3$ |
| 366. | 4-(3-Furyl) | $CH_3$ |
| 367. | 4-(2-Furyl) | $CH_3$ |
| 368. | 4-(2-Pyrrolyl) | $CH_3$ |
| 369. | 4-(2-Thienyl) | $CH_3$ |
| 370. | 4-(Pyridazin-2-yl) | $CH_3$ |
| 371. | 4-(4-Methylthiazol-5-yl) | $CH_3$ |
| 372. | 4-(2-Methyloxazol-4-yl) | $CH_3$ |
| 373. | 4-(Cyclopropyl) | $CH_3$ |
| 374. | 4-(Cyclobutyl) | $CH_3$ |
| 375. | 4-(Cyclopentyl) | $CH_3$ |
| 376. | 4-(Cyclohexyl) | $CH_3$ |
| 377. | 4-(Oxan-4-yl) | $CH_3$ |
| 378. | 4-(1-Methylpiperidin-4-yl) | $CH_3$ |
| 379. | 4-OH, 5-$CF_3$ | $CH_3$ |
| 380. | 4-OH, 5-$CH_3$ | $CH_3$ |
| 381. | 4-OH, 5-$C_2H_5$ | $CH_3$ |
| 382. | 4-OH, 5-CN | $CH_3$ |
| 383. | 4-OH, 5-F | $CH_3$ |
| 384. | 4-OH, 5-Cl | $CH_3$ |
| 385. | 4-OH, 6-$CH_3$ | $CH_3$ |
| 386. | 3-OH | $CH(CH_3)_2$ |
| 387. | 4-OH | $CH(CH_3)_2$ |
| 388. | 5-OH | $CH(CH_3)_2$ |
| 389. | 3-$CH_3$ | $CH(CH_3)_2$ |
| 390. | 4-$CH_3$ | $CH(CH_3)_2$ |
| 391. | 5-$CH_3$ | $CH(CH_3)_2$ |
| 392. | 3-$OCH_3$ | $CH(CH_3)_2$ |
| 393. | 4-$OCH_3$ | $CH(CH_3)_2$ |
| 394. | 5-$OCH_3$ | $CH(CH_3)_2$ |
| 395. | 3-$N(CH_3)_2$ | $CH(CH_3)_2$ |
| 396. | 4-$N(CH_3)_2$ | $CH(CH_3)_2$ |
| 397. | 5-$N(CH_3)_2$ | $CH(CH_3)_2$ |
| 398. | 3-Cl | $CH(CH_3)_2$ |
| 399. | 4-Cl | $CH(CH_3)_2$ |
| 400. | 5-Cl | $CH(CH_3)_2$ |
| 401. | 3-$CF_3$ | $CH(CH_3)_2$ |
| 402. | 4-$CF_3$ | $CH(CH_3)_2$ |
| 403. | 5-$CF_3$ | $CH(CH_3)_2$ |
| 404. | 3-CN | $CH(CH_3)_2$ |
| 405. | 4-CN | $CH(CH_3)_2$ |
| 406. | 5-CN | $CH(CH_3)_2$ |
| 407. | 3-$H_3C$—O—$CH_2$ | $CH(CH_3)_2$ |
| 408. | 4-$H_3C$—O—$CH_2$ | $CH(CH_3)_2$ |
| 409. | 5-$H_3C$—O—$CH_2$ | $CH(CH_3)_2$ |
| 410. | 6-$CH_3$ | $CH(CH_3)_2$ |
| 411. | 4-tert-Butyl | $CH(CH_3)_2$ |
| 412. | 4-Azetidin-1-yl | $CH(CH_3)_2$ |
| 413. | 4-Pyrrolidin-1-yl | $CH(CH_3)_2$ |
| 414. | 4-Piperidin-1-yl | $CH(CH_3)_2$ |
| 415. | 4-Phenyl | $CH(CH_3)_2$ |
| 416. | 4-(1-Methylpyrrol-2-yl) | $CH(CH_3)_2$ |
| 417. | 4-(3-Pyridyl) | $CH(CH_3)_2$ |
| 418. | 4-(3-Thienyl) | $CH(CH_3)_2$ |
| 419. | 4-(4-Fluorophenyl) | $CH(CH_3)_2$ |
| 420. | 4-(4-Pyridyl) | $CH(CH_3)_2$ |
| 421. | 4-(3-Furyl) | $CH(CH_3)_2$ |

TABLE 1-continued

| | R¹, R² | R⁴ |
|---|---|---|
| 422. | 4-(2-Furyl) | CH(CH₃)₂ |
| 423. | 4-(2-Pyrrolyl) | CH(CH₃)₂ |
| 424. | 4-(2-Thienyl) | CH(CH₃)₂ |
| 425. | 4-(Pyridazin-2-yl) | CH(CH₃)₂ |
| 426. | 4-(4-Methylthiazol-5-yl) | CH(CH₃)₂ |
| 427. | 4-(2-Methyloxazol-4-yl) | CH(CH₃)₂ |
| 428. | 4-(Cyclopropyl) | CH(CH₃)₂ |
| 429. | 4-(Cyclobutyl) | CH(CH₃)₂ |
| 430. | 4-(Cyclopentyl) | CH(CH₃)₂ |
| 431. | 4-(Cyclohexyl) | CH(CH₃)₂ |
| 432. | 4-(Oxan-4-yl) | CH(CH₃)₂ |
| 433. | 4-(1-Methylpiperidin-4-yl) | CH(CH₃)₂ |
| 434. | 4-OH, 5-CF₃ | CH(CH₃)₂ |
| 435. | 4-OH, 5-CH₃ | CH(CH₃)₂ |
| 436. | 4-OH, 5-C₂H₅ | CH(CH₃)₂ |
| 437. | 4-OH, 5-CN | CH(CH₃)₂ |
| 438. | 4-OH, 5-F | CH(CH₃)₂ |
| 439. | 4-OH, 5-Cl | CH(CH₃)₂ |
| 440. | 4-OH, 6-CH₃ | CH(CH₃)₂ |
| 441. | 3-OH | CH₂CH₂CH₃ |
| 442. | 4-OH | CH₂CH₂CH₃ |
| 443. | 5-OH | CH₂CH₂CH₃ |
| 444. | 3-CH₃ | CH₂CH₂CH₃ |
| 445. | 4-CH₃ | CH₂CH₂CH₃ |
| 446. | 5-CH₃ | CH₂CH₂CH₃ |
| 447. | 3-OCH₃ | CH₂CH₂CH₃ |
| 448. | 4-OCH₃ | CH₂CH₂CH₃ |
| 449. | 5-OCH₃ | CH₂CH₂CH₃ |
| 450. | 3-N(CH₃)₂ | CH₂CH₂CH₃ |
| 451. | 4-N(CH₃)₂ | CH₂CH₂CH₃ |
| 452. | 5-N(CH₃)₂ | CH₂CH₂CH₃ |
| 453. | 3-Cl | CH₂CH₂CH₃ |
| 454. | 4-Cl | CH₂CH₂CH₃ |
| 455. | 5-Cl | CH₂CH₂CH₃ |
| 456. | 3-CF₃ | CH₂CH₂CH₃ |
| 457. | 4-CF₃ | CH₂CH₂CH₃ |
| 458. | 5-CF₃ | CH₂CH₂CH₃ |
| 459. | 3-CN | CH₂CH₂CH₃ |
| 460. | 4-CN | CH₂CH₂CH₃ |
| 461. | 5-CN | CH₂CH₂CH₃ |
| 462. | 3-H₃C—O—CH₂ | CH₂CH₂CH₃ |
| 463. | 4-H₃C—O—CH₂ | CH₂CH₂CH₃ |
| 464. | 5-H₃C—O—CH₂ | CH₂CH₂CH₃ |
| 465. | 6-CH₃ | CH₂CH₂CH₃ |
| 466. | 4-tert-Butyl | CH₂CH₂CH₃ |
| 467. | 4-Azetidin-1-yl | CH₂CH₂CH₃ |
| 468. | 4-Pyrrolidin-1-yl | CH₂CH₂CH₃ |
| 469. | 4-Piperidin-1-yl | CH₂CH₂CH₃ |
| 470. | 4-Phenyl | CH₂CH₂CH₃ |
| 471. | 4-(1-Methylpyrrol-2-yl) | CH₂CH₂CH₃ |
| 472. | 4-(3-Pyridyl) | CH₂CH₂CH₃ |
| 473. | 4-(3-Thienyl) | CH₂CH₂CH₃ |
| 474. | 4-(4-Fluorophenyl) | CH₂CH₂CH₃ |
| 475. | 4-(4-Pyridyl) | CH₂CH₂CH₃ |
| 476. | 4-(3-Furyl) | CH₂CH₂CH₃ |
| 477. | 4-(2-Furyl) | CH₂CH₂CH₃ |
| 478. | 4-(2-Pyrrolyl) | CH₂CH₂CH₃ |
| 479. | 4-(2-Thienyl) | CH₂CH₂CH₃ |
| 480. | 4-(Pyridazin-2-yl) | CH₂CH₂CH₃ |
| 481. | 4-(4-Methylthiazol-5-yl) | CH₂CH₂CH₃ |
| 482. | 4-(2-Methyloxazol-4-yl) | CH₂CH₂CH₃ |
| 483. | 4-(Cyclopropyl) | CH₂CH₂CH₃ |
| 484. | 4-(Cyclobutyl) | CH₂CH₂CH₃ |
| 485. | 4-(Cyclopentyl) | CH₂CH₂CH₃ |
| 486. | 4-(Cyclohexyl) | CH₂CH₂CH₃ |
| 487. | 4-(Oxan-4-yl) | CH₂CH₂CH₃ |
| 488. | 4-(1-Methylpiperidin-4-yl) | CH₂CH₂CH₃ |
| 489. | 4-OH, 5-CF₃ | CH₂CH₂CH₃ |
| 490. | 4-OH, 5-CH₃ | CH₂CH₂CH₃ |
| 491. | 4-OH, 5-C₂H₅ | CH₂CH₂CH₃ |
| 492. | 4-OH, 5-CN | CH₂CH₂CH₃ |
| 493. | 4-OH, 5-F | CH₂CH₂CH₃ |
| 494. | 4-OH, 5-Cl | CH₂CH₂CH₃ |
| 495. | 4-OH, 6-CH₃ | CH₂CH₂CH₃ |

Particularly preferred compounds are additionally those of the formulae Ib, Ic, Id and Ie,

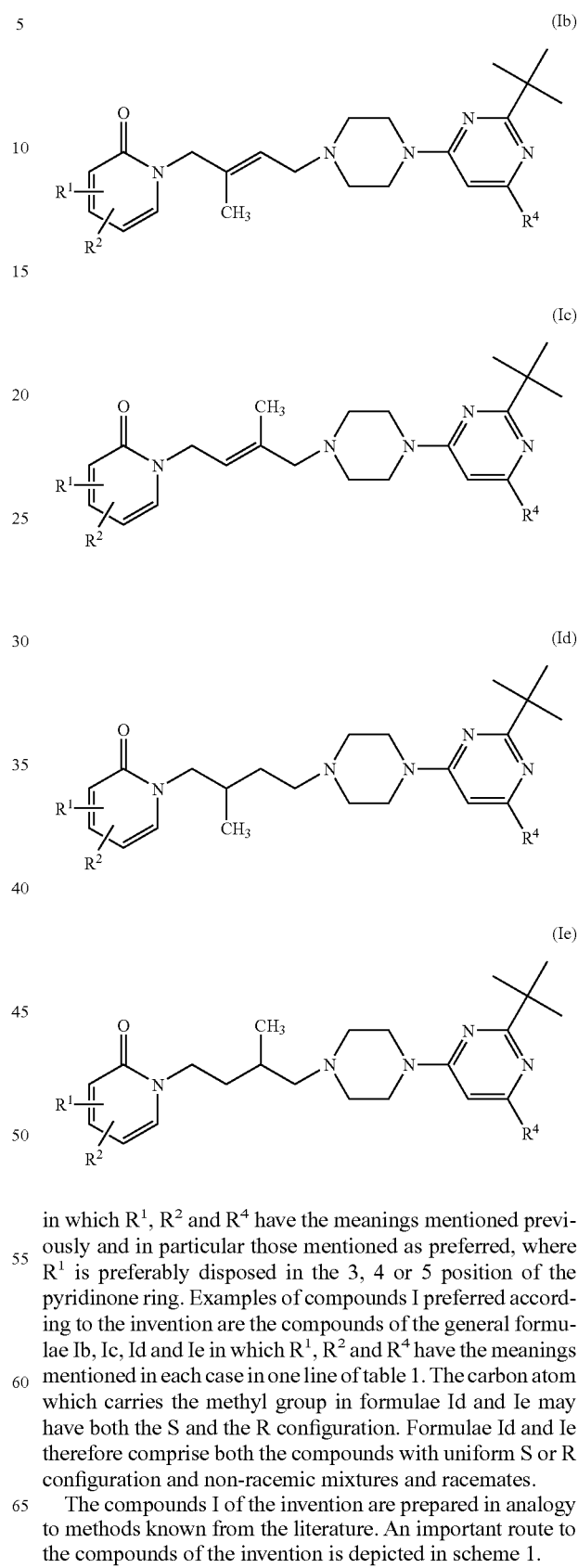

in which $R^1$, $R^2$ and $R^4$ have the meanings mentioned previously and in particular those mentioned as preferred, where $R^1$ is preferably disposed in the 3, 4 or 5 position of the pyridinone ring. Examples of compounds I preferred according to the invention are the compounds of the general formulae Ib, Ic, Id and Ie in which $R^1$, $R^2$ and $R^4$ have the meanings mentioned in each case in one line of table 1. The carbon atom which carries the methyl group in formulae Id and Ie may have both the S and the R configuration. Formulae Id and Ie therefore comprise both the compounds with uniform S or R configuration and non-racemic mixtures and racemates.

The compounds I of the invention are prepared in analogy to methods known from the literature. An important route to the compounds of the invention is depicted in scheme 1.

Scheme 1:

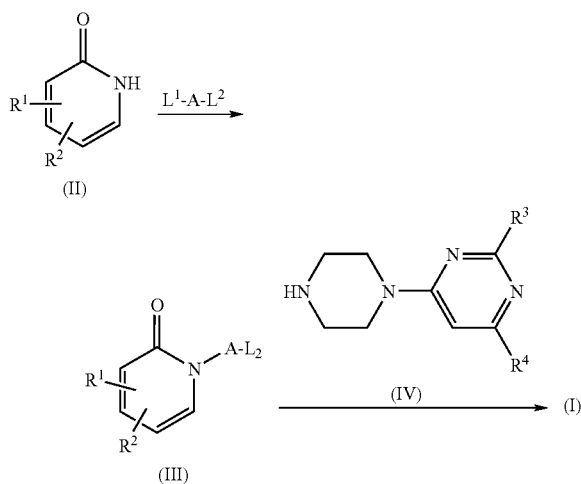

$R^1$, $R^2$, $R^3$, R and A in scheme 1 have the aforementioned meanings. $L^1$ and $L^2$ are nucleophilically displaceable leaving groups. Examples of suitable nucleophilically displaceable leaving groups are halogen, especially chlorine, bromine or iodine, alkyl- and arylsulfonate such as mesylate, tosylate. $L^1$ and $L^2$ are preferably different from one another and differ in reactivity. For example, $L^1$ is bromine or iodine and $L^2$ is chlorine. The reaction conditions required for the reaction correspond to the reaction conditions usual for nucleophilic substitutions.

Compounds of the general formula IV are either known from the literature, e.g. from WO 96/02519, WO 97/25324, WO 99/02503 or from the literature cited in these publications, or can be prepared by the processes described therein.

The pyridinone compounds of the formulae II are known and in some cases commercially available or can be prepared by known processes for pyridinone synthesis as described, for example, in J. Med. Chem. 16(5), 1973, pp. 524-528, J. Org. Chem., 67, 2002, pp. 4304-4308, Bioorg., Med. Chem. Lett, 12, 2002, pp. 3537-3541.

In the compounds I with $R^1$=SH, the thiol group can be converted by standard processes of organic chemistry into other radicals $R^1$. Scheme 2 provides a survey.

Scheme 2:

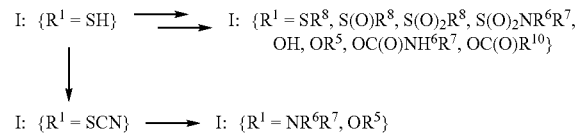

Processes for this purpose are known to the skilled worker and comprise conversion of SH into $SR^8$ by alkylation, oxidation of $SR^8$ to the corresponding $SOR^8$ and $SO_2R^6$ groups, oxidative degradation of SH to OH with optional subsequent alkylation or esterification to give the groups $OR^5$, $OC(O)NR^6R^7$ or $OC(O)R^{10}$.

The halogen atom in the compounds I and in the starting materials of the formula II in which $R^1$ is Cl, Br or I can be replaced by a C-bonded organic radical $R^1$ in a transition metal-catalyzed reaction, e.g. in the presence of elemental Pd or Pd compounds, e.g. in the manner of a Suzuki reaction, of a Stille coupling, or of a Heck reaction. It is possible in particular for compounds I and pyridones I in which $R^1$ is an optionally substituted phenyl ring to be prepared by reacting the corresponding halogen compound I or II ($R^1$=Cl, Br or I) with a borate M[aryl$_4$B] in which M is a cation of an alkali metal, e.g. Na$^+$, and aryl is optionally substituted phenyl, under Suzuki conditions (see Tetrahedron 1997, 53, 14437-50). This modified Suzuki cross-coupling between a halopyridone I or II and the borate normally takes place in aqueous solvents in the presence of a phosphine-free Pd catalyst such as palladium(II) chloride and in the presence of a base. Examples of suitable bases are alkali metal hydroxides such as sodium hydroxide. The halopyridones II and borates are known from the literature.

Unless indicated otherwise, the reactions described above will generally take place in a solvent at a temperature between room temperature and the boiling point of the solvent used. Examples of solvents which can be used are ethers such as diethyl ether, diisopropyl ether, methyl tert-butyl ether or tetrahydrofuran, dimethylformamide, dimethyl sulfoxide, dimethoxyethane, toluene, xylene, acetonitrile, ketones such as acetone or methyl ethyl ketone, or alcohols such as methanol, ethanol or butanol.

The energy of activation necessary for the reaction can be introduced into the reaction mixture by means of microwaves (for reaction with use of microwaves, see Tetrahedron 2001, 57, pp. 9199 et seq., pp. 9225 et seq., and generally "Microwaves in Organic Synthesis", André Loupy (editor), Wiley-VCH 2002).

If desired, a base is present to neutralize the protons liberated during the reaction. Suitable bases comprise inorganic bases such as sodium or potassium carbonate, sodium or potassium bicarbonate, also alcoholates such as sodium methoxide, sodium ethoxide, alkali metal hydrides such as sodium hydride, organometallic compounds such as butyllithium or alkylmagnesium compounds, or organic nitrogen bases such as triethylamine or pyridine. The latter may simultaneously act as solvent.

The crude product is isolated in a conventional way, for example by filtration, removal of the solvent by distillation or extraction from the reaction mixture etc. The resulting compounds can be purified in a conventional way, for example by recrystallization from a solvent, chromatography or conversion into an acid addition salt.

The acid addition salts are prepared in a conventional way by mixing the free base with the appropriate acid, where appropriate in solution in an organic solvent, for example a low molecular weight alcohol such as methanol, ethanol or propanol, an ether such as methyl t-butyl ether or diisopropyl ether, a ketone such as acetone or methyl ethyl ketone or an ester such as ethyl acetate.

The inventive compounds of the formula I are in general highly selective dopamine $D_3$ receptor ligands which, because of their low affinity for other receptors such as $D_1$ receptors, $D_4$ receptors, α1- and/or α2-adrenergic receptors, muscarinergic receptors, histaminic receptors, opiate receptors and, in particular, for dopamine $D_2$ receptors, have fewer side effects than classical neuroleptics which comprise $D_2$ receptor antagonists.

The high affinity of the inventive compounds for $D_3$ receptors is reflected in very, low in vitro $K_i$ values of ordinarily less than 100 nM (nmol/l), frequently less than 50 nM and especially of less than 10 nM. Binding affinities for $D_3$ receptors can for example be determined via the displacement of [$^{125}$I]-iodosulpiride in receptor-binding studies.

Particularly important according to the invention are compounds whose selectivity $K_i(D_2)/K_i(D_3)$ is preferably at least 10, frequently at least 30 and particularly advantageously at least 50. Receptor-binding studies on $D_1$, $D_2$ and $D_4$ receptors can be carried out for example via the displacement of [$^3$H]SCH23390, [$^{125}$I]iodosulpiride and [$^{125}$I]spiperone.

The compounds can, because of their binding profile, be used for the treatment of conditions which respond to dopamine $D_3$ ligands, i.e. they are effective for the treatment of those disorders or conditions where an influencing (modulation) of dopamine $D_3$ receptors leads to an improvement in the clinical condition or to cure of the disease. Examples of such conditions are disorders or conditions of the central nervous system.

Disorders or conditions of the central nervous system mean disorders affecting the spinal cord or, in particular, the brain. The term "disorder" in the sense according to the invention refers to abnormalities which are usually regarded as pathological states or functions and may reveal themselves in the form of particular signs, symptoms and/or dysfunctions. The inventive treatment may be directed at individual disorders, i.e. abnormalities or pathological states, but it is also possible for a plurality of abnormalities, which are causally connected together where appropriate, to be combined into patterns, i.e. syndromes, which can be treated according to the invention.

The disorders which can be treated according to the invention include in particular psychiatric and neurological disorders. These comprise in particular organic disorders, symptomatic disorders included, such as psychoses of the acute exogenous type or associated psychoses with an organic or exogenous cause, e.g. associated with metabolic disorders, infections and endocrinopathies; endogenous psychoses such as schizophrenia and schizotypal and delusional disorders; affective disorders such as depressions, mania and manic/depressive states; and combined forms of the disorders described above; neurotic and somatoform disorders, and disorders associated with stress; dissociative disorders, e.g. deficits, clouding and splitting of consciousness and personality disorders; disorders of attention and waking/sleeping behavior, such as behavioral disorders and emotional disorders starting in childhood and adolescence, e.g. hyperactivity in children, intellectual deficits, especially attention deficit disorders, disorders of memory and cognition, e.g. learning and memory impairment (impaired cognitive function), dementia, narcolepsy and sleeping disorders, e.g. restless legs syndrome; developmental disorders; anxiety states; delirium; disorders of the sex life, e.g. male impotence; eating disorders, e.g. anorexia or bulimia; addiction; and other undefined psychiatric disorders.

The disorders which can be treated according to the invention also include parkinsonism and epilepsy and, in particular, the affective disorders associated therewith.

Addictive disorders include the psychological disorders and behavioral disorders caused by the abuse of psychotropic substances such as pharmaceuticals or drugs, and other addictive disorders such as, for example, compulsive gambling (impulse control disorders not elsewhere classified). Examples of addictive substances are: opioids (e.g. morphine, heroin, codeine); cocaine; nicotine; alcohol; substances which interact with the GABA chloride channel complex, sedatives, hypnotics or tranquilizers, for example benzodiazepines; LSD; cannabinoids; psychomotor stimulants such as 3,4-methylenedioxy-N-methylamphetamine (Ecstasy); amphetamine and amphetamine-like substances such as methylphenidate or other stimulants, including caffeine. Addictive substances requiring particular attention are opioids, cocaine, amphetamine or amphetamine-like substances, nicotine and alcohol.

With a view to the treatment of addictive disorders, the inventive compounds of the formula I which are particularly preferred are those which themselves have no psychotropic effect. This can also be observed in a test on rats which reduce the self-administration of psychotropic substances, for example cocaine, after administration of compounds which can be used according to the invention.

According to a further aspect of the present invention, the inventive compounds are suitable for the treatment of disorders, the causes of which can at least in part be attributed to an abnormal activity of dopamine $D_3$ receptors.

According to another aspect of the present invention, the treatment is directed in particular at those disorders which can be influenced by a binding of, preferably exogenously added, binding partners (ligands) to dopamine $D_3$ receptors in the sense of an expedient medical treatment.

The conditions which can be treated with the inventive compounds are frequently characterized by a progressive development, i.e. the states described above change over the course of time, the severity usually increasing and, where appropriate, states possibly interchanging or other states being added to previously existing states.

The inventive compounds can be used to treat a large number of signs, symptoms and/or dysfunctions associated with the disorders of the central nervous system and in particular the aforementioned states. These include for example a distorted relation to reality, lack of insight and the ability to comply with the usual social norms and demands of life, changes in behavior, changes in individual urges such as hunger, sleep, thirst etc. and in mood, disorders of memory and association, personality changes, especially emotional lability, hallucinations, ego disturbances, incoherence of thought, ambivalence, autism, depersonalization or hallucinations, delusional ideas, staccato speech, absence of associated movement, small-step gait, bent posture of trunk and limbs, tremor, mask-like face, monotonous speech, depression, apathy, deficient spontaneity and irresolution, reduced association ability, anxiety, nervous agitation, stammering, social phobia, panic disorders, withdrawal syndromes associated with dependence, expansive syndromes, states of agitation and confusion, dysphoria, dyskinetic syndromes and tic disorders, e.g. Huntington's chorea, Gilles de la Tourette syndrome, vertigo syndromes, e.g. peripheral postural, rotational and vestibular vertigo, melancholia, hysteria, hypochondria and the like.

A treatment in the sense according to the invention includes not only the treatment of acute or chronic signs, symptoms and/or dysfunctions but also a preventive treatment (prophylaxis), in particular as recurrence or episode prophylaxis. The treatment may be symptomatic, for example directed at suppression of symptom. It may take place short-term, be directed at the medium term or may also be a long-term treatment, for example as part of maintenance therapy.

The inventive compounds are preferably suitable for the treatment of disorders of the central nervous system, especially for the treatment of affective disorders; neurotic disorders, stress disorders and somatoform disorders and psychoses and specifically for the treatment of schizophrenia and depression. Owing to their high selectivity in relation to the $D_3$ receptor, the inventive compounds are also for the treatment of renal function disorders, especially of renal function disorders caused by diabetes mellitus (see WO 00/67847).

The inventive use of the described compounds comprises a method within the scope of the treatment. This entails the individual to be treated, preferably a mammal, in particular a human or agricultural or domestic animal, being given an effective amount of one or more compounds, usually formulated in accordance with pharmaceutical and veterinary practice. Whether such a treatment is indicated, and the form it is to take, depends on the individual case and is subject to a medical assessment (diagnosis) which takes account of the signs, symptoms and/or dysfunctions present, the risks of developing certain signs, symptoms and/or dysfunctions, and other factors.

The treatment usually takes place by administration once or more than once a day, where appropriate together or alternately with other active ingredients or active ingredient-containing products, so that an individual to be treated is given a daily dose preferably of about 0.1 to 1000 mg/kg of body weight on oral administration or of about 0.1 to 100 mg/kg of body weight on parenteral administration.

The invention also relates to the production of pharmaceutical compositions for the treatment of an individual, preferably a mammal, in particular a human or agricultural or domestic animal. Thus, the ligands are usually administered in the form of pharmaceutical compositions which comprise a pharmaceutically acceptable excipient with at least one ligand of the invention and, where appropriate, further active ingredients. These compositions can be administered for example by the oral, rectal, transdermal, subcutaneous, intravenous, intramuscular or intranasal route.

Examples of suitable pharmaceutical formulations are solid pharmaceutical forms such as oral powders, dusting powders, granules, tablets, especially film-coated tablets, pastilles, sachets, cachets, sugar-coated tablets, capsules such as hard and soft gelatin capsules, suppositories or vaginal pharmaceutical forms, semisolid pharmaceutical forms such as ointments, creams, hydrogels, pastes or patches, and liquid pharmaceutical forms such as solutions, emulsions, especially oil-in-water emulsions, suspensions, for example lotions, preparations for injection and infusion, eye drops and ear drops. Implanted delivery devices can also be used to administer compounds of the invention. A further possibility is also to use liposomes or microspheres.

The compositions are produced by mixing or diluting compounds of the invention usually with an excipient. Excipients may be solid, semisolid or liquid materials which serve as vehicle, carrier or medium for the active ingredient.

Suitable excipients are listed in the relevant pharmaceutical monographs. The formulations may additionally comprise pharmaceutically acceptable carriers or conventional excipients such as lubricants; wetting agents; emulsifying and suspending agents; preservatives; antioxidants; antiirritants; chelating agents; tablet-coating aids; emulsion stabilizers; film formers; gel formers; odor-masking agents; masking flavors; resins; hydrocolloids; solvents; solubilizers; neutralizers; permeation promoters; pigments; quaternary ammonium compounds; refatting and superfatting agents; ointment, cream or oil bases; silicone derivatives; spreading aids; stabilizers; sterilants; suppository bases; tablet excipients, such as binders, fillers, lubricants, disintegrants or coatings; propellants; desiccants; opacifiers; thickeners; waxes; plasticizers; white oils. An arrangement concerning this is based on expert knowledge as set forth for example in Fiedler, H. P., Lexikon der Hilfsstoffe für Pharmazie, Kosmetik und angrenzende Gebiete, 4th edition, Aulendorf: ECV-Editio-Kantor-Verlag, 1996.

The following examples serve to illustrate the invention without limiting it.

The nuclear magnetic resonance spectral properties (NMR) relate to chemical shifts (δ) expressed in parts per million (ppm). The relative area for the shifts in the $^1$H NMR spectrum corresponds to the number of hydrogen atoms for a particular functional type in the molecule. The nature of the shift in terms of multiplicity is indicated as singlet (s), broad singlet (s. br.), doublet (d), broad doublet (d br.), triplet (t), broad triplet (t br.), quartet (q), quintet (quint.), multiplet (m).

I. PREPARATION EXAMPLES

Example 1

1-(4-{4-[2-tert-Butyl-6-(trifluoromethyl)pyrimidin-4-yl]piperazin-1-yl}butyl)-4-methylpyridin-2(1H)-one 1.1 1-(4-Chlorobutyl)-4-methylpyridin-2(1H)-one A mixture of 2-hydroxy-4-methylpyridine (1.50 g, 13.75 mmol) and potassium carbonate (1.90 g, 13.75 mmol) in 13 ml of methanol were stirred at room temperature for 15 minutes and then 1-bromo-4-chlorobutane (3.54 g, 20.62 mmol) and a spatula tip of potassium iodide were added thereto. The reaction mixture was heated to reflux for 6 hours and then stirred at room temperature for 12 hours. Water was then added to the reaction mixture, and the aqueous mixture was extracted with dichloromethane. Drying of the organic phase and removal of the desiccant by filtration was followed by concentration of the organic phase in vacuo. Flash chromatography of resulting residue on silica gel (eluent: $CH_2Cl_2$/$CH_3OH$: 98:2) afforded 2.0 g of 1-(4-chlorobutyl)-4-methylpyridin-2(1H)-one.

$^1$H NMR (400 MHz, $CDCl_3$) δ (ppm): 7.13 (1H, d), 6.37 (1H, s), 6.02 (1H, d), 3.95 (2H, t), 3.56 (2H, t), 2.17 (3H, s), 1.90 (2H, quint.), 1.83 (2H, quint.).

1.2 1-(4-{4-[2-tert-Butyl-6-(trifluoromethyl)pyrimidin-4-yl]piperazin-1-yl}butyl)-4-methylpyridin-2(1H)-one 1-(4-Chlorobutyl)-4-methylpyridin-2(1H)-one (0.99 g, 4.96 mmol) from Example 1.1, 2-tert-butyl-4-piperazin-1-yl-6-(trifluoromethyl)pyrimidine (1.36 g, 4.71 mmol; prepared as described in DE 19735410) and triethylamine (1.51 g, 14.87 mmol) in 25 ml of dimethyl sulfoxide were stirred at 100° C. for 5 hours. Water was then added to the reaction mixture, and the aqueous mixture was extracted twice with tert-butyl methyl ether. The organic phase was extracted three times with a saturated aqueous sodium chloride solution and three times with a 5% aqueous citric acid solution. The aqueous phase was then made alkaline and extracted three times with tert-butyl methyl ether. The combined organic phases were dried over $Na_2SO_4$ and, after removal of the desiccant by filtration, concentrated. The resulting oily residue (1.99 g) was purified by chromatography on silica gel (eluent: $CH_2Cl_2$/$CH_3OH$: 96.5:3.5), resulting in 1.29 g of the title compound.

$^1$H NMR (500 MHz, $CDCl_3$) δ (ppm): 7.15 (1H, d), 6.59 (1H, s), 6.34 (1H, s), 6.00 (1H, d), 3.92 (2H, t), 3.70 (4H, s br.), 2.50 (4H, t), 2.41 (2H, t), 2.18 (3H, s), 1.80 (2H, quint.), 1.57 (2H, quint.), 1.33 (9H, s).

Example 2

1-(4-{4-[2-tert-Butyl-6-(trifluoromethyl)pyrimidin-4-yl]piperazin-1-yl}butyl)-5-(trifluoromethyl)pyridin-2(1H)-one 2.1 1-(4-Chlorobutyl)-5-(trifluoromethyl)pyridin-2(1H)-one 1.95 g of the title compound were obtained by reacting 5-(trifluoromethyl)-2-pyridinol (1.63 g, 10 mmol) with 1-bromo-4-chlorobutane in analogy to Example 1.1.

ESI-MS: $[M+H^+]$=254.1.

2.2 1-(4-{4-[2-tert-Butyl-6-(trifluoromethyl)pyrimidin-4-yl]piperazin-1-yl}butyl)-5-(trifluoromethyl)pyridin-2(1H)-one 0.39 g of the title compound was obtained in analogy to Example 1.2 by reacting 1-(4-chlorobutyl)-5-(trifluoromethyl)pyridin-2(1H)-one (0.65 g, 2.56 mmol) from Example 2.1.

$^1$H NMR (500 MHz, CDCl$_3$) δ (ppm): 7.66 (1H, s), 7.45 (1H, d), 6.63 (1H, d), 6.58 (1H, s), 4.00 (2H, t), 3.73 (4H, s br.), 2.51 (4H, t), 2.43 (2H, t), 1.83 (2H, quint.), 1.60 (2H, quint.), 1.32 (9H, s).

Example 3

4-(2-tert-Butyl-6-propylpyrimidin-4-yl)-1-[4-(4-methyl-2-oxopyridin-1(2H)-yl)butyl]piperazin-1-ium chloride 0.74 g of the title compound was obtained by reacting 1-(4-chlorobutyl)-4-methylpyridin-2(1H)-one (2.50 mmol, 0.50 g) from Example 1.1 with 2-tert-butyl-4-piperazin-1-yl-6-propylpyrimidine (0.62 g, 2.38 mmol; preparation as described in DE 19735410) in analogy to Example 1.2.

ESI-MS: 427.5, [M+H$^+$]=426.5, 213.8.

Example 4

4-(2-tert-Butyl-6-isopropylpyrimidin-4-yl)-1-[4-(4-methyl-2-oxopyridin-1(2H)-yl)butyl]piperazin-1-ium chloride 0.38 g of the title compound was obtained by reacting 1-(4-chlorobutyl)-4-methylpyridin-2(1H)-one (1.25 mmol, 0.25 g) from Example 1.1 with 2-tert-butyl-4-piperazin-1-yl-6-isopropylpyrimidine (0.31 g, 1.19 mmol; prepared as described in DE 19735410) in analogy to Example 1.2.

ESI-MS: 427.4, [M+H$^+$]=426.2, 213.8.

Example 5

1-{4-[4-(2-tert-Butyl-6-propylpyrimidin-4-yl)piperazin-1-yl]butyl}-3-methoxy-1H-pyridin-2-one

5.1 1-(4-Chlorobutyl)-3-methoxy-1H-pyridin-2-one

3-Methoxy-1H-pyridin-2-one (20 mmol, 2.00 g) in 100 ml of N,N-dimethylformamide was added dropwise over the course of 10 minutes to a suspension of sodium hydride (20 mmol, 0.74 g, 60%, deoiled) in N,N-dimethylformamide (100 ml) at 10° C., and the mixture was then stirred at room temperature for 1 hour. Subsequently, 1-bromo-4-chlorobutane (20 mmol, 3.19 g) in 40 ml of N,N-dimethylformamide was added dropwise. The reaction mixture was then stirred at 95° C. After the reaction mixture had been concentrated, the remaining oil was suspended in diethyl ether. The resulting suspension was filtered and the filtrate was washed three times with water and then three times with a saturated aqueous sodium chloride solution. Drying of the organic phase over sodium sulfate was followed by removal of the desiccant by filtration and concentration. The resulting residue contained a mixture of O-alkylated and N-alkylated compound. Chromatography of the residue on silica gel (eluent: CH$_2$Cl$_2$/CH$_3$OH: 0-2%) afforded 1.75 g of the title compound.

$^1$H NMR (400 MHz, CDCl$_3$) δ (ppm): 6.88 (1H, d), 6.60 (1H, d), 6.12 (1H, t), 4.02 (2H, t), 3.81 (3H, s), 3.57 (1H, t), 3.44 (1H, t), 2.02-1.72 (4H, m).

5.2 1-{4-[4-(2-tert-Butyl-6-propylpyrimidin-4-yl)piperazin-1-yl]butyl}-3-methoxy-1H-pyridin-2-one A mixture of 1-(4-chlorobutyl)-3-methoxy-1H-pyridin-2-one (0.93 mmol, 0.20 g) from Example 5.1, 2-tert-butyl-4-piperazin-1-yl-6-propylpyrimidine (0.93 mmol, 0.24 g; prepared as described in DE 19735410), sodium bromide (4.64 mmol, 0.48 g), ethyldiisopropylamine (9.09 mmol, 1.17 g) and N-methylpyrrolidinone (0.5 ml) was heated at 120° C. for 6 hours. The resulting suspension was filtered with suction and the filtrate was concentrated. The residue obtained in this way was taken up in ethyl acetate/water. The aqueous mixture was adjusted to pH 5.5 with sodium bicarbonate and the aqueous mixture was extracted several times with diethyl ether. The organic phase was then dried, the desiccant was removed by filtration, and the organic phase was concentrated under reduced pressure. Chromatography of the residue on silica gel (eluent: CH$_2$Cl$_2$/CH$_3$OH (0-2%) afforded 0.24 g of the title compound.

ESI-MS: [M+H$^+$]=442.4, 221.6.

Example 6

1-{4-[4-(2-tert-Butyl-6-trifluoromethylpyrimidin-4-yl)piperazin-1-yl]butyl}-3-methoxy-1H-pyridin-2-one 0.25 g of the title compound was obtained by reacting 1-(4-chlorobutyl)-3-methoxy-1H-pyridin-2-one (0.93 mmol, 0.20 g) from Example 5.1 with 2-tert-butyl-4-piperazin-1-yl-6-(trifluoromethyl)pyrimidine (0.93 mmol, 0.27 g; prepared as described in DE 19735410) in analogy to Example 5.2.

ESI-MS: [M+H$^+$]=468.2;

$^1$H NMR (400 MHz, DMSO-d$_6$) δ (ppm): 7.27 (1H, d), 6.80 (1H, d), 6.15 (1H, t), 4.66 (2H, br.), 3.90 (2H, t), 3.57-3.36 (4H, m), 3.17-2.95 (4H, m), 1.64 (4H, m sym.), 1.29 (9H, s).

Example 7

1-{4-[4-(2-tert-Butyl-6-propylpyrimidin-4-yl)piperazin-1-yl]butyl}-3-methyl-1H-pyridin-2-one

7.1 1-(4-Chlorobutyl)-3-methyl-1H-pyridin-2-one 1.98 g of the title compound were obtained by reacting 3-methyl-1H-pyridin-2-one (17.96 mmol, 2.00 g) with 1-bromo-4-chlorobutane in analogy to Example 1.1.

ESI-MS: [M+H$^+$]=200.05;

$^1$H NMR (400 MHz, CDCl$_3$) δ (ppm): 7.19 (1H, d), 7.13 (1H, d), 6.10 (1H, t), 3.99 (2H, t), 3.58 (2H, t), 2.16 (3H, s), 2.05-1.75 (4H, m).

7.2 1-{4-[4-(2-tert-Butyl-6-propylpyrimidin-4-yl)piperazin-1-yl]butyl}-3-methyl-1H-pyridin-2-one 0.19 g of the title compound was obtained by reacting 1-(4-chlorobutyl)-3-methyl-1H-pyridin-2-one (1.00 mmol, 0.20 g) from Example 7.1 with 2-tert-butyl-4-piperazin-1-yl-6-propylpyrimidine (1.00 mmol, 0.26 g; prepared as described in DE 19735410) in analogy to Example 5.2.

ESI-MS: [M+H$^+$]=426.4, 213.8.

Example 8

4-(2-tert-Butyl-6-propylpyrimidin-4-yl)-1-[4-(4-chloro-2-oxo-2H-pyridin-1-yl)butyl]-piperazine as hydrochloride

8.1 4-Chloro-1-(4-chlorobutyl)-1H-pyridin-2-one 0.20 g of the title compound was obtained by reacting 4-chloropyridin-2-ol (1.54 mmol, 0.20 g) with 1-bromo-4-chlorobutane in analogy to Example 1.1.
$^1$H NMR (400 MHz, CDCl$_3$) δ (ppm): 7.20 (1H, d), 6.60 (1H, s), 6.20 (1H, d), 3.94 (2H, t), 3.58 (2H, t), 1.90 (2H, quint.), 1.81 (2H, quint.).

8.2 4-(2-tert-Butyl-6-propylpyrimidin-4-yl)-1-[4-(4-chloro-2-oxo-2H-pyridin-1-yl)butyl]-piperazine hydrochloride 0.16 g of the title compound was obtained by reacting 4-chloro-1-(4-chlorobutyl)-1H-pyridin-2-one (0.45 mmol, 0.10 g) from Example 8.1 with 2-tert-butyl-4-piperazin-1-yl-6-propylpyrimidine (0.43 mmol, 0.11 g; prepared as described in DE 19735410) in analogy to Example 5.2.
ESI-MS: 448.2, 446.3, 224.6, 223.6;
$^1$H NMR (400 MHz, CDCl$_3$) δ (ppm): 7.20 (1H, d), 6.60 (1H, s), 6.18 (1H, d), 6.12 (1H, s), 3.95 (2H, t), 3.60 (4H, s br.), 2.60-2.33 (8H, m including 2.53 (2H, t), 2.40 (2H, t)), 1.83-1.49 (6H, m), 1.33 (9H, s), 0.97 (3H, t).

Example 9

4-(2-tert-Butyl-6-trifluoromethylpyrimidin-4-yl)-1-[4-(4-chloro-2-oxo-2H-pyridin-1-yl)butyl]piperazine as hydrochloride 0.12 g of the title compound was obtained by reacting 4-chloro-1-(4-chlorobutyl)-1H-pyridin-2-one (0.45 mmol, 0.10 g) from Example 8.1 with 2-tert-butyl-4-piperazin-1-yl-6-(trifluoromethyl)pyrimidine (0.43 mmol, 0.11 g; prepared as described in DE 19735410) in analogy to Example 5.2.
ESI-MS: 474.2, 472.2, 237.4, 236.6;
$^1$H NMR (400 MHz, CDCl$_3$) δ (ppm): 7.20 (1H, d), 6.60 (1H, s), 6.58 (1H, s), 6.19 (1H, d), 3.94 (2H, t), 3.68 (4H, s br.), 2.47 (2H, t), 2.39 (2H, t), 1.77 (2H, quint.), 1.65 (2H+H$_2$O, quint.), 1.33 (9H, s).

Example 10

1-{4-[4-(2-tert-Butyl-6-propylpyrimidin-4-yl)piperazin-1-yl]butyl}-4-hydroxy-1H-pyridin-2-one

10.1 1-(4-Chlorobutyl)-4-hydroxy-1H-pyridin-2-one 1.30 g of the title compound were obtained by reacting 4-hydroxy-1H-pyridin-2-one (18.00 mmol, 2.00 g) with 1-bromo-4-chlorobutane in analogy to Example 1.1.

10.2 1-{4-[4-(2-tert-Butyl-6-propylpyrimidin-4-yl)piperazin-1-yl]butyl}-4-hydroxy-1H-pyridin-2-one 0.40 g of the title compound was obtained by reacting 1-(4-chlorobutyl)-4-hydroxy-1H-pyridin-2-one (2.48 mmol, 0.50 g) from Example 10.1 with 2-tert-butyl-4-piperazin-1-yl-6-propylpyrimidine (2.48 mmol, 0.65 g; prepared as described in DE 19735410) in analogy to Example 5.2.
ESI-MS: [M+H$^+$]=428.4, 214.6;
$^1$H NMR (400 MHz, DMSO-d$_6$) δ (ppm): 11.93 (1H, s br.), 7.17 (1H, d), 6.12 (1H, s), 5.95 (1H, d), 5.87 (1H, s), 3.97 (2H, t), 3.62 (4H, s br.), 2.63-2.36 (8H, m), 1.81 (2H, quint.), 1.66 (4H+H$_2$O, quint.), 1.33 (9H, s), 0.96 (3H, t).

Example 11

1-{4-[4-(2-tert-Butyl-6-trifluoromethylpyrimidin-4-yl)piperazin-1-yl]butyl}-3-methyl-1H-pyridin-2-one 0.34 g of the title compound was obtained by reacting 1-(4-chlorobutyl)-3-methyl-1H-pyridin-2-one (1.50 mmol, 0.30 g) from Example 7.1 with 2-tert-butyl-4-piperazin-1-yl-6-(trifluoromethyl)pyrimidine (1.53 mmol, 0.44 g; prepared as described in DE 19735410) in analogy to Example 5.2.
ESI-MS: [M+H$^+$]=452.2, 226.6;
$^1$H NMR (400 MHz, DMSO-d$_6$) δ (ppm): 7.50 (1H, d), 7.27 (1H, d), 7.03 (1H, s), 6.11 (1H, t), 3.87 (2H, t), 3.68 (4H, s br.), 2.57-2.35 (6H, m including 2.36 (2H, t)), 1.98 (3H, s), 1.62 (2H, quint.), 1.43 (2H, quint.), 1.25 (9H, s).

Example 12

1-{4-[4-(2-tert-Butyl-6-trifluoromethylpyrimidin-4-yl)piperazin-1-yl]butyl}-4-hydroxy-1H-pyridin-2-one 0.30 g of the title compound was obtained by reacting 1-(4-chlorobutyl)-4-hydroxy-1H-pyridin-2-one (1.24 mmol, 0.25 g) from Example 10.1 with 2-tert-butyl-4-piperazin-1-yl-6-(trifluoromethyl)pyrimidine (1.24 mmol, 0.36 g; prepared as described in DE 19735410) in analogy to Example 5.2.
ESI-MS: [M+H$^+$]=454.2, 227.6;
$^1$H NMR (400 MHz, DMSO-d$_6$) δ (ppm): 12.04 (1H, s br.), 7.17 (1H, d), 6.58 (1H, s), 5.95 (1H, d), 5.86 (1H, s), 3.99 (2H, t), 3.71 (4H, s br.), 2.52 (4H, s br.), 2.43 (2H, t), 1.82 (2H, quint.), 1.77-1.51 (2H+H$_2$O, m), 1.35 (9H, s).

Example 13

1-{4-[4-(2-tert-Butyl-6-trifluoromethylpyrimidin-4-yl)piperazin-1-yl]butyl}-3-trifluoromethyl-1H-pyridin-2-one

13.1 1-(4-Chlorobutyl)-3-trifluoromethyl-1H-pyridin-2-one 1.10 g of the title compound were obtained by reacting 3-trifluoromethyl-1H-pyridin-2-one (6.13 mmol, 1.00 g) with 1-bromo-4-chlorobutane in analogy to Example 1.1.
ESI-MS (N-alk.): [M+H$^+$]=254.1;
$^1$H NMR (400 MHz, CDCl$_3$) δ (ppm): 7.73 (1H, d), 7.47 (1H, d), 6.24 (1H, t), 4.03 (2H, t), 3.60 (2H, t), 1.95 (2H, q), 1.82 (2H, q).
ESI-MS (O-alk.): [M+Na$^+$]=276.1, 256.1, [M+H$^+$]=254.1.

13.2 1-{4-[4-(2-tert-Butyl-6-trifluoromethylpyrimidin-4-yl)piperazin-1-yl]butyl}-3-trifluoromethyl-1H-pyridin-2-one 0.17 g of the title compound was obtained by reacting 1-(4-chlorobutyl)-3-trifluoromethyl-1H-pyridin-2-one (0.59 mmol, 0.15 g) from Example 13.1 with 2-tert-butyl-4-piperazin-1-yl-6-(trifluoromethyl)pyrimidine (0.59 mmol, 0.17 g; prepared as described in DE 19735410) in analogy to Example 5.2.
ESI-MS: [M+H$^+$]=506.2, 253.6;

¹H NMR (400 MHz, CDCl₃) δ (ppm): 7.75 (1H, d), 7.50 (1H, d), 6.68 (1H, s), 6.22 (1H, t), 4.01 (2H, t), 3.68 (4H, s br.), 2.51 (4H, s br.), 2.43 (2H, t), 1.84 (2H, quint.), 1.72-1.46 (2H+H₂O, s br.), 1.33 (9H, s).

Example 14

1-{4-[4-(2-tert-Butyl-6-propylpyrimidin-4-yl)piperazin-1-yl]butyl}-3-trifluoromethyl-1H-pyridin-2-one 0.15 g of the title compound was obtained by reacting 1-(4-chlorobutyl)-3-trifluoromethyl-1H-pyridin-2-one (0.59 mmol, 0.15 g) from Example 13.1 with 2-tert-butyl-4-piperazin-1-yl-6-propylpyrimidine (0.59 mmol, 0.16 g; prepared as described in DE 19735410) in analogy to Example 5.2.

ESI-MS: [M+H⁺]=480.2, 240.6;

¹H NMR (400 MHz, DMSO-d₆) δ (ppm): 8.04 (1H, d), 7.91 (1H, d), 6.43 (1H, s), 6.35 (1H, t), 3.97 (2H, t), 3.57 (4H, s br.), 2.56-2.27 (6H, m including 2.33 (2H, t)), 1.74-1.55 (4H, m), 1.45 (2H, quint.), 1.25 (9H, s), 0.90 (3H, t).

Example 15

4-(2-tert-Butyl-6-propylpyrimidin-4-yl)-1-[4-(2-oxo-4-trifluoromethyl-2H-pyridin-1-yl)butyl]piperazine as fumarate 15.1 1-(4-Chlorobutyl)-4-trifluoromethyl-1H-pyridin-2-one The title compound was obtained in a yield of 0.45 g by reacting 4-trifluoromethyl-1H-pyridin-2-one (3.07 mmol, 0.50 g) with 1-bromo-4-chlorobutane in analogy to the preparation method from Example 1.1.

15.2 4-(2-tert-Butyl-6-propylpyrimidin-4-yl)-1-[4-(2-oxo-4-trifluoromethyl-2H-pyridin-1-yl)butyl]-piperazine as fumarate The title compound was obtained in a yield of 0.24 g by reacting 1-(4-chlorobutyl)-4-trifluoromethyl-1H-pyridin-2-one (0.63 mmol, 0.16 g) with 2-tert-butyl-4-piperazin-1-yl-6-propylpyrimidine (0.60 mmol, 0.16 g, preparation according to DE 19735410) in analogy to the preparation method from Example 5.2.

ESI-MS: [M+H⁺]=480.25, 240.65;

¹H NMR (400 MHz, DMSO-d₆) δ (ppm): 7.96 (1H, d), 6.76 (1H, s), 6.47 (1H, m), 6.44 (1H, s), 3.96 (2H, t), 3.56 (4H, s), 2.58-2.23 (8H, m), 1.74-1.38 (6H, m), 1.25 (9H, s), 0.89 (3H, t).

Example 16

4-(2-tert-Butyl-6-trifluoromethylpyrimidin-4-yl)-1-[4-(2-oxo-4-trifluoromethyl-2H-pyridin-1-yl)butyl]piperazine as fumarate The title compound was obtained in a yield of 0.12 g by reacting 1-(4-chlorobutyl)-4-trifluoromethyl-1H-pyridin-2-one (0.63 mmol, 0.16 g) with 2-tert-butyl-4-piperazin-1-yl-6-trifluoromethylpyrimidine (0.60 mmol, 0.17 g, preparation according to DE 19735410) in analogy to the preparation method in Example 1.2.

ESI-MS: [M+Na⁺]=528.2, 507.2, [M+H⁺]=506.1, 253.6;

Example 17

4-(2-tert-Butyl-6-propylpyrimidin-4-yl)-1-[4-(5-chloro-2-oxo-2H-pyridin-1-yl)butyl]-piperazine as fumarate 17.1: 5-Chloro-1-(4-chlorobutyl)-1H-pyridin-2-one 1.63 g of the title compound were obtained by reacting 5-chloro-1H-pyridin-2-one (15.44 mmol, 2.00 g) with 1-bromo-4-chlorobutane in analogy to Example 1.1.

ESI-MS: [M+H⁺]=221.9, 220.9, 219.9;

17.2 4-(2-tert-Butyl-6-propylpyrimidin-4-yl)-1-[4-(5-chloro-2-oxo-2H-pyridin-1-yl)butyl]-piperazine as fumarate obtained in a yield of 0.35 g by reacting 5-chloro-1-(4-chlorobutyl)-1H-pyridin-2-one (0.91 mmol, 0.20 g) with 2-tert-butyl-4-piperazin-1-yl-6-propylpyrimidine (0.82 mmol, 0.21 g, preparation according to DE 19735410) in analogy to the method from Example 1.2.

ESI-MS: 448.2, [M+H⁺]=446.3, 244.4, 223.6;

¹H NMR (400 MHz, DMSO-d₆) δ (ppm): 7.96 (1H, d), 7.46 (1H, dd), 6.46-6.35 (2H, m), 3.86 (2H, t), 3.58 (4H, s br.), 2.45 (6H, s br.), 1.63 (4H, sext.), 1.43 (2H, quint.), 1.24 (9H, s), 0.90 (3H, t).

Example 18

4-(2-tert-Butyl-6-trifluoromethylpyrimidin-4-yl)-1-[4-(5-chloro-2-oxo-2H-pyridin-1-yl)butyl]piperazine as fumarate The title compound was obtained in a yield of 0.23 g by reacting 5-chloro-1-(4-chlorobutyl)-1H-pyridin-2-one (0.91 mmol, 0.20 g) and 2-tert-butyl-4-piperazin-1-yl-6-trifluoromethylpyrimidine (0.82 mmol, 0.24 g, preparation according to DE 19735410 in analogy to the method from Example 1.2.

ESI-MS: 474.1, [M+H⁺]=472.1, 237.4, 236.6;

¹H NMR (500 MHz, DMSO-d₆) δ (ppm): 7.97 (1H, s), 7.44 (1H, d), 7.04 (1H, s), 6.41 (1H, d), 3.86 (2H, t), 3.70 (4H, s br.), 2.44 (4H, m sym.), 2.34 (2H, t), 1.65 (2H, quint.), 1.44 (2H, quint.), 1.28 (9H, s).

Example 19

1-{4-[4-(2-tert-Butyl-6-trifluoromethylpyrimidin-4-yl)piperazin-1-yl]butyl}-4-phenyl-1H-pyridin-2-one 19.1: 1-(4-Chlorobutyl)-4-phenyl-1H-pyridin-2-one 34 mg of the title compound were obtained by reacting 4-phenyl-1H-pyridin-2-one (0.41 mmol, 71.0 mg, prepared from 4-chloro-1H-pyridin-2-one according to Tetrahedron 1997, 53, pp. 14437-50) with 1-bromo-4-chlorobutane in analogy to Example 1.1.

ESI-MS: 202.1, [M+H⁺]=200.1;

19.2: 1-{4-[4-(2-tert-Butyl-6-trifluoromethylpyrimidin-4-yl)piperazin-1-yl]butyl}-4-phenyl-1H-pyridin-2-one The title compound was obtained in a yield of 12 mg by reacting 1-(4-chlorobutyl)-4-phenyl-1H-pyridin-2-one (0.13 mmol, 34.0 mg) with 2-tert-butyl-4-piperazin-1-yltrifluoromethylpyrimidine (0.13 mmol, 37.5 mg, preparation according to DE 19735410) in analogy to the method from Example 1.2.

ESI-MS: [M+Na$^+$]=536.2, 515.2, [M+H$^+$]=514.2, 257.6;
$^1$H NMR (400 MHz, DMSO-d$_6$) δ (ppm): 7.77 (1H, d), 7.72 (2H, d), 7.53-7.41 (3H, m), 7.03 (1H, s br.), 6.66 (1H, s), 6.58 (1H, d), 3.93 (2H, t), 3.70 (4H, s br.), 2.41 (4H, s br.), 2.33 (2H, m), 1.68 (2H, quint.), 1.48 (2H, m), 1.27 (9H, s).

Example 20

4-(2-tert-Butyl-6-propylpyrimidin-4-yl)-1-[4-(6-methyl-2-oxo-2H-pyridin-1-yl)butyl]-piperazine as fumarate 20.1 1-(4-Chlorobutyl)-6-methyl-1H-pyridin-2-one 0.40 g of the title compound was obtained by reacting 6-methyl-1H-pyridin-2-one (18.33 mmol, 2.00 g) with 1-bromo-4-chlorobutane in analogy to Example 1.1.
ESI-MS: 202.1, [M+H$^+$]=200.1;

20.2 4-(2-tert-Butyl-6-propylpyrimidin-4-yl)-1-[4-(6-methyl-2-oxo-2H-pyridin-1-yl)-butyl]-piperazine as fumarate The title compound was obtained in a yield of 0.18 g by reacting 1-(4-chlorobutyl)-6-methyl-1H-pyridin-2-one (0.75 mmol, 0.15 mg) with 2-tert-butyl-4-piperazin-1-yl-6-propylpyrimidine (0.67 mmol, 0.18 g, preparation according to DE 19735410) in analogy to the method from Example 1.2.
ESI-MS: 427.4, [M+H$^+$]=426.4, 213.6;
$^1$H NMR (500 MHz, DMSO-d$_6$) δ (ppm): 7.24 (1H, m sym.), 6.43 (1H, s), 6.21 (1H, d), 6.06 (1H, d), 3.96 (2H, t), 3.59 (4H, s br.), 2.47 (8H, m), 2.37 (3H, s), 1.66-1.49 (6H, m), 1.27 (9H, s), 0.90 (3H, t).

Example 21

4-(2-tert-Butyl-6-trifluoromethylpyrimidin-4-yl)-1-[4-(6-methyl-2-oxo-2H-pyridin-1-yl)butyl]piperazine as fumarate The title compound was obtained in a yield of 0.24 g by reacting 1-(4-chlorobutyl)-6-methyl-1H-pyridin-2-one 0.75 mmol, 0.15 mg) with 2-tert-butyl-4-piperazin-1-yl-6-trifluoromethylpyrimidine (0.68 mmol, 0.19 g, preparation according to DE 19735410) in analogy to the method from Example 1.2.
ESI-MS: [M+H$^+$]=452.2, 226.6;
$^1$H NMR (500 MHz, DMSO-d$_6$) δ (ppm): 7.23 (1H, m sym.), 7.03 (1H, s), 6.21 (1H, d), 6.08 (1H, d), 3.96 (2H, t), 3.72 (4H, s br.), 2.46 (4H, m), 2.41-2.34 (5H, m), 1.59 (2H, quint.), 1.52 (2H, quint.), 1.28 (9H, s).

II EXAMPLES OF PHARMACEUTICAL ADMINISTRATION FORMS

| Tablets | |
|---|---|
| Tablets of the following composition are compressed in a tablet press in a conventional way: | |
| 40 mg | of substance of example 2 |
| 120 mg | of corn starch |
| 13.5 mg | of gelatin |
| 45 mg | of lactose |
| 2.25 mg | of Aerosil ® (chemically pure silica in submicroscopically fine distribution) |
| 6.75 mg | of potato starch (as 6% strength paste) |
| | Sugar-coated tablets |
| 20 mg | of substance of example 2 |
| 60 mg | of core composition |
| 70 mg | of sugar-coating composition |

The core composition consists of 9 parts of corn starch, 3 parts of lactose and 1 part of vinylpyrrolidone/vinyl acetate 60:40 copolymer. The sugar-coating composition consists of 5 parts of sucrose, 2 parts of corn starch, 2 parts of calcium carbonate and 1 part of talc. The sugar-coated tablets produced in this way are subsequently provided with an enteric coating.

III. BIOLOGICAL INVESTIGATIONS

Receptor Binding Studies

The substance to be tested was dissolved either in methanol/Chremophor® (BASF-AG) or in dimethyl sulfoxide and then diluted with water to the desired concentration.

III.1 Dopamine D$_3$ Receptor:

The mixture (0.250 ml) is composed of membranes from ~10$^6$ HEK-293 cells with stably expressed human dopamine D$_3$ receptors, 0.1 nM [$^{125}$I]-iodosulpiride and incubation buffer (total binding) or with additional test substance (inhibition plot) or 1 μM spiperone (nonspecific binding). Triplicate mixtures were carried out.

The incubation buffer contained 50 mM Tris, 120 mM NaCl, 5 mM KCl, 2 mM CaCl$_2$, 2 mM MgCl$_2$ and 0.1% bovine serum albumin, 10 μM quinolone, 0.1% ascorbic acid (prepared fresh each day). The buffer was adjusted to pH 7.4 with HCl.

III.2 Dopamine D$_{2L}$ Receptor:

The mixture (1 ml) was composed of membranes from ~10$^6$ HEK-293 cells with stably expressed human dopamine D$_{2L}$ receptors (long isoform) and 0.01 nM [$^{125}$I]-iodospiperone and incubation buffer (total binding) or with additional test substance (inhibition plot) or 1 μM haloperidol (nonspecific binding). Triplicate mixtures were carried out.

The incubation buffer contained 50 mM Tris, 120 mM NaCl, 5 mM KCl, 2 mM CaCl$_2$, 2 mM MgCl$_2$ and 0.1% bovine serum albumin. The buffer was adjusted to pH 7.4 with HCl.

III.3 Measurement and Evaluation:

After incubation at 25° C. for 60 minutes, the mixtures were filtered under vacuum through Whatman GF/B glass fiber filters using a cell harvester. The filters were transferred by a filter transfer system into scintillation vials. After addition of 4 ml of Ultima Gold® (Packard), the samples were shaken for one hour and then the radioactivity was counted in a beta counter (Packard, Tricarb 2000 or 2200CA). The cp values were converted into dpm by means of a standard quench series with the aid of the instrument's own program.

Evaluation of the inhibition plots took place by iterative nonlinear regression analysis using the Statistical Analysis System (SAS) similar to the "LIGAND" program described by Munson and Rodbard.

In these assays, the inventive compounds show very good affinities for the $D_3$ receptor (<100 nM, frequently <50 nM and in particular >10 nM) and bind selectively to the $D_3$ receptor.

The results of the binding assays are indicated in table 2.

TABLE 2

| Example | $K_i$ ($D_3$) [nM] | Selectivity vs. $D_2L$* |
|---------|-----|-----|
| 1 | 0.76 | 82 |
| 3 | 0.84 | 137 |
| 5 | 1.20 | 51 |
| 6 | 2.20 | 74 |
| 7 | 1.25 | 129 |
| 11 | 2.31 | 74 |
| 19 | 7.89 | 63 |

*$K_i(D_{2L})/K_i(D_3)$

We claim:

1. A pyridin-2-one compound of the formula I

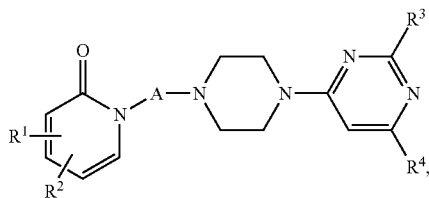

in which

A is a 4- to 6-membered hydrocarbon chain which may have 1 or 2 methyl groups as substituents, in which 1 or 2 carbon atoms may be replaced by oxygen, a carbonyl group or sulfur, and in which the hydrocarbon chain may have a double bond or a triple bond;

$R^1$, $R^2$ are independently of one another hydrogen, CN, $NO_2$, halogen, $OR^5$, $NR^6R^7$, $C(O)NR^6R^7$, O—C(O)$NR^6R^7$, $SR^8$, $SOR^8$, $SO_2R^8$, $SO_2NR^6R^7$, $COOR^9$, O—C(O)$R^{10}$, $COR^{10}$, $C_1$-$C_6$-alkyl, $C_1$-$C_6$-haloalkyl, $C_2$-$C_6$-alkenyl, $C_2$-$C_6$-alkynyl, $C_2$-$C_6$-haloalkenyl, $C_3$-$C_6$-cycloalkyl, 4- to 6-membered heterocyclyl having 1, 2 or 3 heteroatoms selected from O, S and N, which may have 1, 2 or 3 substituents which are selected independently of one another from $C_1$-$C_4$-alkyl, $C_1$-$C_4$-alkoxy, $NR^6R^7$, CN, OH, $C_1$-$C_2$-fluoroalkyl or halogen, phenyl which may have 1, 2 or 3 substituents which are selected independently of one another from $C_1$-$C_4$-alkyl, $C_1$-$C_4$-alkoxy, $NR^6R^7$, OH, CN, $C_1$-$C_2$-fluoroalkyl or halogen, $C_1$-$C_6$-alkyl which has a substituent which is selected from $OR^5$, $NR^6R^7$, $C(O)NR^6R^7$, O—C(O)$NR^6R^7$, $SR^8$, $SOR^8$, $SO_2R^8$, $SO_2NR^6R^7$, $COOR^9$, O—C(O)$R^{10}$, $COR^{10}$, $C_3$-$C_6$-cycloalkyl, 5- or 6-membered heterocyclyl having 1, 2 or 3 heteroatoms selected from O, S and N, and phenyl, where phenyl and heterocyclyl may have 1, 2 or 3 substituents which are selected independently of one another from $C_1$-$C_4$-alkyl, $C_1$-$C_4$-alkoxy, $NR^6R^7$, CN, OH, $C_1$-$C_2$-fluoroalkyl or halogen, $C_2$-$C_6$-alkenyl which has a substituent selected from $OR^5$, $NR^6R^7$, $C(O)NR^6R^7$, O—C(O)$NR^6R^7$, $SR^8$, $SOR^8$, $SO_2R^8$, $SO_2NR^6R^7$, $COOR^9$, O—C(O)$R^{10}$, $COR^{10}$, $C_3$-$C_6$-cycloalkyl, 5- or 6-membered heterocyclyl having 1, 2 or 3 heteroatoms selected from O, S and N, and phenyl, where phenyl and heterocyclyl in turn may have 1, 2 or 3 substituents which are selected independently of one another from $C_1$-$C_4$-alkyl, $C_1$-$C_4$-alkoxy, $NR^6R^7$, OH, CN, $C_1$-$C_2$-fluoroalkyl or halogen;

$R^3$, $R^4$ are independently of one another $OR^5$, $NR^6R^7$, CN, $C_1$-$C_6$-alkyl which is optionally substituted one or more times by OH, $C_1$-$C_4$-alkoxy, halogen or phenyl which in turn may have 1, 2 or 3 substituents selected from $C_1$-$C_4$-alkyl, $C_1$-$C_4$-alkoxy, $NR^6R^7$, OH, CN, $C_1$-$C_2$-fluoroalkyl or halogen, or $C_2$-$C_6$-alkenyl, $C_2$-$C_6$-alkynyl, $C_3$-$C_6$-cycloalkyl, $C_4$-$C_{10}$-bicycloalkyl, $C_6$-$C_{10}$-tricycloalkyl, where the last 5 groups mentioned may optionally be substituted one or more times by halogen or $C_1$-$C_4$-alkyl, or halogen, CN, $C_1$-$C_4$-alkoxy, 5- or 6-membered heterocyclyl having 1, 2 or 3 heteroatoms selected from O, S and N, and phenyl, where phenyl and heterocyclyl may optionally have 1, 2 or 3 substituents which are selected independently of one another from $C_1$-$C_4$-alkyl, $C_1$-$C_4$-alkoxy, $NR^6R^7$, CN, $C_1$-$C_2$,-fluoroalkyl and halogen;

$R^5$, $R^6$, $R^7$, $R^8$, $R^9$ and $R^{10}$ are independently of one another H, $C_1$-$C_6$-alkyl which is optionally substituted by OH, $C_1$-$C_4$-alkoxy or phenyl which in turn may have 1, 2 or 3 substituents selected from $C_1$-$C_4$-alkyl, $C_1$-$C_4$-alkoxy, $NR^6R^7$, OH, CN, $C_1$-$C_2$-fluoroalkyl or halogen, or $C_1$-$C_6$-haloalkyl or phenyl which in turn may have 1, 2 or 3 substituents selected from $C_1$-$C_4$-alkyl, $C_1$-$C_4$-alkoxy, $NR^6R^7$, OH, CN, $C_1$-$C_2$-fluoroalkyl or halogen, where $R^7$ may also be a $COR^{11}$ group, and where $R^6$ with $R^7$ may also, together with the nitrogen to which they are bonded, form a 4-, 5- or 6-membered, saturated or unsaturated heterocycle which may have a further heteroatom selected from O, S and $NR^{12}$ as ring member, where $R^{12}$ is hydrogen or $C_1$-$C_4$-alkyl, and which may be substituted by 1, 2, 3 or 4 alkyl groups; and $R^{11}$ is hydrogen, $C_1$-$C_4$-alkyl or phenyl which is optionally substituted by 1, 2 or 3 radicals which are selected independently of one another from $C_1$-$C_4$-alkyl, $C_1$-$C_4$-alkoxy, $NR^6R^7$, CN, $C_1$-$C_2$-fluoroalkyl or halogen;

and the tautomers of the compound I, the physiologically acceptable salts of the compound I and the physiologically acceptable salts of the tautomers of the compound I.

2. A pyridin-2-one compound according to claim 1, in which $R^3$ is $C_1$-$C_6$-alkyl, and $R^4$ is selected from $C_1$-$C_6$-alkyl, $C_3$-$C_6$-cycloalkyl which optionally has 1 or 2 substituents selected from chlorine and methyl, and $C_1$-$C_2$-fluoroalkyl.

3. A pyridin-2-one compound according to claim 2, in which $R^3$ is branched alkyl having 3, 4 or 5 C atoms or is $C_3$-$C_6$-cycloalkyl.

4. A pyridin-2-one compound according to claim 2, in which $R^4$ is trifluoromethyl or $C_3$-$C_4$-alkyl.

5. A pyridin-2-one compound according to claim 2, in which $R^4$ is cyclopropyl, cyclobutyl, cyclopentyl or 1-methylcyclopropyl.

6. A pyridin-2-one compound according to claim 1, in which at least one of the radicals $R^1$ or $R^2$ is different from hydrogen.

7. A pyridin-2-one compound according to claim 6, in which $R^1$ is selected from halogen, $OR^5$, $NR^6R^7$, $C_1$-$C_4$-alkyl which is optionally substituted by OH, $C_1$-$C_4$-alkoxy or halogen, or aromatic 5- or 6-membered heterocyclyl having 1, 2 or 3 heteroatoms selected from O, S and N, which may have 1, 2 or 3 substituents which are selected independently of one another from $C_1$-$C_4$-alkyl, $C_1$-$C_4$-alkoxy, $NR^6R^7$, CN, OH, $C_1$-$C_2$-fluoroalkyl or halogen, and phenyl which may have 1, 2 or 3 substituents which are selected independently of one another from $C_1$-$C_4$-alkyl, $C_1$-$C_4$-alkoxy, $NR^6R^7$, OH, CN, $C_1$-$C_2$-fluoroalkyl or halogen.

8. A pyridin-2-one compound according to claim 7, in which $R^1$ is selected from phenyl, OH, chlorine, methyl, methoxy and trifluoromethyl.

9. A pyridin-2-one compound according to claim 1, in which $R^2$ is hydrogen.

10. A pyridin-2-one compound according to claim 1, in which A is butane-1,4-diyl.

11. A pharmaceutical composition comprising at least one compound according to claim 1 and/or salt thereof, optionally together with physiologically acceptable carriers and/or excipients.

12. A method for treating a D3 receptor related condition comprising administering an effective amount of at least one compound of claim 1 to a subject in need thereof, wherein the condition is selected from the group consisting of Parkinson's disease, anxiety, schizophrenia, and depression.

* * * * *